US012631651B2

(12) United States Patent \
Fan et al.

(10) Patent No.: US 12,631,651 B2 \
(45) Date of Patent: **\*May 19, 2026**

(54) SYSTEMS AND METHODS FOR GENERATING DROPLETS AND PERFORMING DIGITAL ANALYSES

(71) Applicant: Countable Labs, Inc., Palo Alto, CA (US)

(72) Inventors: Hei Mun Christina Fan, Palo Alto, CA (US); Janice Hoiyi Lai, Mountain View, CA (US); Sixing Li, Mountain View, CA (US); Stephen P.A. Fodor, Palo Alto, CA (US); Eleen Yee Lam Shum, San Carlos, CA (US)

(73) Assignee: Countable Labs, Inc., Palo Alto, CA (US)

( \* ) Notice: Subject to any disclaimer, the term of this patent is extended or adjusted under 35 U.S.C. 154(b) by 0 days.

This patent is subject to a terminal disclaimer.

(21) Appl. No.: 19/400,892

(22) Filed: Nov. 25, 2025

(65) Prior Publication Data

US 2026/0086098 A1 Mar. 26, 2026

Related U.S. Application Data

(63) Continuation of application No. 19/063,118, filed on Feb. 25, 2025, now Pat. No. 12,540,948, which is a (Continued)

(51) Int. Cl.
| | |
|---|---|
| *G01N 33/68* | (2006.01) |
| *C12Q 1/6844* | (2018.01) |
| *G01N 21/64* | (2006.01) |

(52) U.S. Cl.
CPC ......... *G01N 33/689* (2013.01); *C12Q 1/6844* (2013.01); *G01N 21/645* (2013.01); *G01N 21/6486* (2013.01); *G01N 2021/6482* (2013.01)

(58) Field of Classification Search
None
See application file for complete search history.

(56) References Cited

U.S. PATENT DOCUMENTS

| | | | |
|---|---|---|---|
| 2,825,313 | A | 3/1958 | Sidney et al. |
| 3,480,616 | A | 11/1969 | Osipow et al. |
| | | (Continued) | |

FOREIGN PATENT DOCUMENTS

| | | | |
|---|---|---|---|
| CN | 86106153 | A | 6/1987 |
| CN | 1089361 | A | 7/1994 |
| | | (Continued) | |

OTHER PUBLICATIONS

Berrocal, Edouard et al.: Light Sheet Fluorescence microscopic Imaging for High-resolution Visualization of Spray Dynamics. International Journal of Spray and Combustion Dynamics 10(1):86-98 (2018).

(Continued)

*Primary Examiner* — Xiaoyun R Xu

(74) *Attorney, Agent, or Firm* — Wilson Sonsini Goodrich & Rosati

(57) ABSTRACT

This disclosure provides for devices, methods, and systems for generating a plurality of droplets within a collecting container at an extremely high rate (e.g., of at least 1 million droplets per minute, etc.), each of the plurality of droplets comprising an aqueous mixture for a digital analysis, wherein upon generation, the plurality of droplets is stabilized in position within a region of the collecting container. The inventions enable partitioning of samples for digital analyses at unprecedented rates, where readout of signals from targets within such partitions can still be achieved in accordance with various assays.

23 Claims, 13 Drawing Sheets

System 100

Related U.S. Application Data continuation of application No. 18/948,248, filed on Nov. 14, 2024, now Pat. No. 12,270,815, which is a continuation of application No. 18/646,572, filed on Apr. 25, 2024, now Pat. No. 12,265,088, which is a continuation of application No. 17/711,417, filed on Apr. 1, 2022, now Pat. No. 12,000,842, which is a continuation of application No. PCT/US2022/018994, filed on Mar. 4, 2022.

(60) Provisional application No. 63/157,292, filed on Mar. 5, 2021.

(56) References Cited

U.S. PATENT DOCUMENTS

| | | | |
|---|---|---|---|
| 3,644,333 A | 2/1972 | Osipow et al. |
| 4,683,058 A | 7/1987 | Lyman et al. |
| 5,216,033 A | 6/1993 | Pereira et al. |
| 5,707,613 A | 1/1998 | Hill |
| 5,753,241 A | 5/1998 | Ribier et al. |
| 5,925,338 A | 7/1999 | Karassik et al. |
| 6,120,778 A | 9/2000 | Simonnet |
| 6,121,055 A | 9/2000 | Hargreaves |
| 6,329,164 B1 | 12/2001 | Goodwin, Jr. |
| 6,379,682 B1 | 4/2002 | Tchinnis et al. |
| 6,387,357 B1 | 5/2002 | Chopra et al. |
| 6,403,069 B1 | 6/2002 | Chopra et al. |
| 7,041,481 B2 | 5/2006 | Anderson et al. |
| 7,622,076 B2 | 11/2009 | Davies et al. |
| 7,772,287 B2 | 8/2010 | Higuchi et al. |
| RE41,780 E | 9/2010 | Anderson et al. |
| 7,888,017 B2 | 2/2011 | Quake et al. |
| 7,901,939 B2 | 3/2011 | Ismagliov et al. |
| RE43,365 E | 5/2012 | Anderson et al. |
| 8,296,076 B2 | 10/2012 | Fan et al. |
| 8,304,193 B2 | 11/2012 | Ismagilov et al. |
| 8,329,407 B2 | 12/2012 | Ismagilov et al. |
| 8,535,889 B2 | 9/2013 | Larson et al. |
| RE44,596 E | 11/2013 | Stroun et al. |
| 8,614,061 B2 | 12/2013 | Brabetz et al. |
| 8,658,430 B2 | 2/2014 | Miller et al. |
| 8,663,920 B2 | 3/2014 | Saxonov et al. |
| 8,765,382 B2 | 7/2014 | Drmanac |
| 8,798,341 B2 | 8/2014 | Baudry et al. |
| 8,871,444 B2 | 10/2014 | Griffiths et al. |
| 8,877,442 B2 | 11/2014 | Quake et al. |
| 8,889,083 B2 | 11/2014 | Ismagilov et al. |
| 8,889,093 B2 | 11/2014 | Malhotra et al. |
| 8,951,939 B2 | 2/2015 | Saxonov et al. |
| 8,962,820 B2 | 2/2015 | Brabetz et al. |
| 8,968,659 B2 | 3/2015 | Davies et al. |
| 9,012,390 B2 | 4/2015 | Holtze et al. |
| 9,029,083 B2 | 5/2015 | Griffiths et al. |
| 9,039,273 B2 | 5/2015 | Weitz et al. |
| RE45,539 E | 6/2015 | Anderson et al. |
| 9,074,242 B2 | 7/2015 | Larson et al. |
| 9,089,844 B2 | 7/2015 | Hiddessen et al. |
| 9,126,160 B2 | 9/2015 | Ness et al. |
| 9,127,310 B2 | 9/2015 | Larson et al. |
| 9,186,643 B2 | 11/2015 | Griffiths et al. |
| 9,216,392 B2 | 12/2015 | Hindson et al. |
| 9,217,173 B2 | 12/2015 | Engel et al. |
| 9,217,175 B2 | 12/2015 | Regan et al. |
| 9,222,115 B2 | 12/2015 | Marble et al. |
| 9,273,308 B2 | 3/2016 | Link et al. |
| 9,347,095 B2 | 5/2016 | Regan et al. |
| 9,399,797 B2 | 7/2016 | Hutchison et al. |
| 9,400,242 B2 | 7/2016 | Allano et al. |
| 9,410,151 B2 | 8/2016 | Link et al. |
| 9,441,266 B2 | 9/2016 | Larson et al. |
| 9,446,360 B2 | 9/2016 | Mazutis |
| 9,492,797 B2 | 11/2016 | Makarewicz et al. |
| 9,500,664 B2 | 11/2016 | Ness et al. |
| 9,523,116 B2 | 12/2016 | Tzonev et al. |
| 9,556,475 B2 | 1/2017 | Regan et al. |
| RE46,322 E | 2/2017 | Anderson et al. |
| 9,562,837 B2 | 2/2017 | Link |
| 9,580,750 B2 | 2/2017 | Parsons et al. |
| 9,580,751 B2 | 2/2017 | Hahn et al. |
| 9,592,506 B2 | 3/2017 | Ismagilov et al. |
| 9,597,644 B2 | 3/2017 | Davies et al. |
| 9,610,239 B2 | 4/2017 | Feng et al. |
| 9,631,230 B2 | 4/2017 | Davies et al. |
| 9,636,682 B2 | 5/2017 | Hiddessen et al. |
| 9,649,635 B2 | 5/2017 | Hiddessen et al. |
| 9,695,468 B2 | 7/2017 | Hindson et al. |
| 9,708,654 B2 | 7/2017 | Hunicke-Smith et al. |
| 9,719,140 B2 | 8/2017 | Fan et al. |
| 9,738,931 B2 | 8/2017 | Hahn et al. |
| 9,745,617 B2 | 8/2017 | Larson et al. |
| 9,758,535 B2 | 9/2017 | Chia et al. |
| 9,764,322 B2 | 9/2017 | Hiddessen et al. |
| 9,788,564 B2 | 10/2017 | Bromley |
| 9,803,226 B2 | 10/2017 | Diehl et al. |
| 9,839,893 B2 | 12/2017 | Ismagilov et al. |
| 9,845,496 B2 | 12/2017 | Regan et al. |
| 9,850,515 B2 | 12/2017 | McCoy et al. |
| 9,857,303 B2 | 1/2018 | Griffiths et al. |
| 9,885,643 B2 | 2/2018 | Pautz et al. |
| 9,896,722 B2 | 2/2018 | Link |
| 9,902,992 B2 | 2/2018 | Talasaz et al. |
| 9,919,277 B2 | 3/2018 | Griffiths et al. |
| 9,925,501 B2 | 3/2018 | Griffiths et al. |
| 9,926,593 B2 | 3/2018 | Ehrich et al. |
| 9,970,052 B2 | 5/2018 | Do et al. |
| 10,011,865 B2 | 7/2018 | Link |
| RE47,080 E | 10/2018 | Anderson et al. |
| 10,113,196 B2 | 10/2018 | Ryan et al. |
| 10,125,392 B2 | 11/2018 | Drmanac |
| 10,130,950 B2 | 11/2018 | Hung et al. |
| 10,150,786 B2 | 12/2018 | Chia et al. |
| 10,161,007 B2 | 12/2018 | Abate et al. |
| 10,316,873 B2 | 6/2019 | Weitz et al. |
| 10,416,164 B2 | 9/2019 | Poola |
| 10,428,369 B2 | 10/2019 | Miller et al. |
| 10,443,086 B2 | 10/2019 | White et al. |
| 10,512,910 B2 | 12/2019 | Colston, Jr. et al. |
| 10,537,503 B2 | 1/2020 | Lei et al. |
| 10,551,382 B2 | 2/2020 | Link et al. |
| 10,604,789 B2 | 3/2020 | Regan et al. |
| 10,612,081 B2 | 4/2020 | Hutchison et al. |
| 10,612,086 B2 | 4/2020 | Ehrich et al. |
| 10,619,192 B2 | 4/2020 | Chiu et al. |
| 10,626,451 B2 | 4/2020 | Davies et al. |
| 10,639,598 B2 | 5/2020 | Griffiths et al. |
| 10,676,786 B2 | 6/2020 | Davies et al. |
| 10,745,762 B2 | 8/2020 | Abate et al. |
| 10,748,290 B2 | 8/2020 | Adiga |
| 10,927,407 B2 | 2/2021 | Link |
| 10,967,338 B2 | 4/2021 | Davies et al. |
| 11,001,896 B2 | 5/2021 | Abate et al. |
| 11,007,849 B2 | 5/2021 | Csordas et al. |
| 11,084,039 B2 | 8/2021 | Davies et al. |
| 11,085,070 B2 | 8/2021 | Regan et al. |
| 11,130,128 B2 | 9/2021 | Ness et al. |
| RE48,788 E | 10/2021 | Anderson et al. |
| 11,162,136 B1 | 11/2021 | Fan et al. |
| 11,199,532 B2 | 12/2021 | Handique et al. |
| 11,203,787 B2 | 12/2021 | Abate et al. |
| 11,242,558 B2 | 2/2022 | Fan et al. |
| 11,254,968 B2 | 2/2022 | Larson et al. |
| 11,278,898 B2 | 3/2022 | Ismagilov et al. |
| 11,447,817 B2 | 9/2022 | Fan et al. |
| 11,494,914 B2 | 11/2022 | Adiga |
| 11,499,181 B2 | 11/2022 | Regan et al. |
| 11,542,546 B2 | 1/2023 | Fan et al. |
| 11,650,404 B2 | 5/2023 | Meyer et al. |
| 11,814,619 B2 | 11/2023 | Shum et al. |
| 11,834,714 B2 | 12/2023 | Shum et al. |
| 12,000,842 B2 | 6/2024 | Fan et al. |
| 12,031,175 B2 | 7/2024 | Larson et al. |
| 12,252,745 B2 | 3/2025 | Shum et al. |
| 12,265,088 B2 | 4/2025 | Fan et al. |

(56) References Cited

U.S. PATENT DOCUMENTS

| | | | |
|---|---|---|---|
| 12,270,815 | B2 | 4/2025 | Fan et al. |
| 2004/0081633 | A1 | 4/2004 | Mercier et al. |
| 2006/0128883 | A1 | 6/2006 | Garrison et al. |
| 2008/0182910 | A1 | 7/2008 | Qiu et al. |
| 2009/0239308 | A1 | 9/2009 | Dube et al. |
| 2010/0173394 | A1 | 7/2010 | Colston, Jr. et al. |
| 2012/0258516 | A1 | 10/2012 | Schultz et al. |
| 2012/0322058 | A1 | 12/2012 | Regan et al. |
| 2014/0272996 | A1 | 9/2014 | Bemis |
| 2016/0026758 | A1 | 1/2016 | Jabara et al. |
| 2016/0158752 | A1 | 6/2016 | Chiou et al. |
| 2016/0231324 | A1 | 8/2016 | Zhao et al. |
| 2017/0321270 | A1 | 11/2017 | Haque et al. |
| 2018/0057889 | A1 | 3/2018 | Haber et al. |
| 2018/0066305 | A1 | 3/2018 | Weitz et al. |
| 2018/0092847 | A1 | 4/2018 | Schutt et al. |
| 2018/0136114 | A1 | 5/2018 | Delattre et al. |
| 2018/0251817 | A1 | 9/2018 | Do et al. |
| 2018/0346984 | A1 | 12/2018 | Quake et al. |
| 2019/0119723 | A1 | 4/2019 | Cumbie et al. |
| 2019/0255531 | A1 | 8/2019 | Hindson et al. |
| 2019/0323073 | A1 | 10/2019 | Lin et al. |
| 2019/0358625 | A1 | 11/2019 | Huang et al. |
| 2019/0360020 | A1 | 11/2019 | Huang et al. |
| 2019/0361027 | A1 | 11/2019 | Poola |
| 2019/0367991 | A1 | 12/2019 | Yu et al. |
| 2020/0002748 | A1 | 1/2020 | Miller et al. |
| 2020/0010876 | A1 | 1/2020 | Macdonald et al. |
| 2020/0037638 | A1 | 2/2020 | Faraci et al. |
| 2020/0208212 | A1 | 7/2020 | Ehrich et al. |
| 2020/0254400 | A1 | 8/2020 | Griffiths et al. |
| 2020/0354772 | A1 | 11/2020 | Davies et al. |
| 2020/0360928 | A1 | 11/2020 | Ismagilov et al. |
| 2021/0262020 | A1 | 8/2021 | Link |
| 2021/0349027 | A1 | 11/2021 | Fei et al. |
| 2021/0388426 | A1 | 12/2021 | Wang et al. |
| 2021/0388446 | A1 | 12/2021 | Abate et al. |
| 2022/0008914 | A1 | 1/2022 | Hiddessen et al. |
| 2022/0040701 | A1 | 2/2022 | Davies et al. |
| 2022/0186308 | A1 | 6/2022 | Fan et al. |
| 2022/0213530 | A1 | 7/2022 | Larson et al. |
| 2022/0280941 | A1 | 9/2022 | Fan et al. |
| 2022/0339620 | A1 | 10/2022 | Huang et al. |
| 2022/0355292 | A1 | 11/2022 | Hindson et al. |
| 2022/0362764 | A1 | 11/2022 | Hindson et al. |
| 2022/0411857 | A1 | 12/2022 | Fan et al. |
| 2023/0029710 | A1 | 2/2023 | Lai et al. |
| 2023/0057343 | A1 | 2/2023 | Do et al. |
| 2023/0074085 | A1 | 3/2023 | Shum et al. |
| 2023/0086845 | A1 | 3/2023 | Larson et al. |
| 2023/0100349 | A1 | 3/2023 | Fei et al. |
| 2023/0212561 | A1 | 7/2023 | Shum et al. |
| 2023/0220447 | A1 | 7/2023 | Samuels et al. |
| 2023/0287482 | A1 | 9/2023 | Fan et al. |
| 2023/0340627 | A1 | 10/2023 | Tsigankov et al. |
| 2024/0079376 | A1 | 3/2024 | Suwito et al. |
| 2024/0301492 | A1 | 9/2024 | Mazloom et al. |
| 2026/0002210 | A1 | 1/2026 | Shum |

FOREIGN PATENT DOCUMENTS

| | | |
|---|---|---|
| CN | 2612943 Y | 4/2004 |
| CN | 1758405 A | 4/2006 |
| CN | 101904802 A | 12/2010 |
| CN | 103145346 A | 6/2013 |
| CN | 103649813 A | 3/2014 |
| CN | 104111242 A | 10/2014 |
| CN | 104237186 A | 12/2014 |
| CN | 104284970 A | 1/2015 |
| CN | 104407436 A | 3/2015 |
| CN | 104630202 A | 5/2015 |
| CN | 104741156 A | 7/2015 |
| CN | 104741158 A | 7/2015 |
| CN | 104815709 A | 8/2015 |
| CN | 104846100 A | 8/2015 |
| CN | 105854965 A | 8/2016 |
| CN | 106053346 A | 10/2016 |
| CN | 106076443 A | 11/2016 |
| CN | 106459585 A | 2/2017 |
| CN | 107119145 A | 9/2017 |
| CN | 207062288 U | 3/2018 |
| CN | 108135813 A | 6/2018 |
| CN | 109060736 A | 12/2018 |
| CN | 109234363 A | 1/2019 |
| EP | 1505151 B1 | 5/2008 |
| EP | 2370596 A1 | 10/2011 |
| EP | 2534267 A2 | 12/2012 |
| EP | 2364369 B1 | 7/2015 |
| EP | 2954102 A1 | 12/2015 |
| EP | 2516680 B1 | 4/2016 |
| EP | 3024948 A1 | 6/2016 |
| EP | 2385143 B1 | 7/2016 |
| EP | 2478119 B1 | 7/2017 |
| EP | 2534267 B1 | 4/2018 |
| EP | 2825313 B1 | 5/2018 |
| EP | 3341508 A1 | 7/2018 |
| EP | 2954102 B1 | 12/2018 |
| EP | 3024948 B1 | 1/2020 |
| EP | 3033445 B1 | 1/2020 |
| EP | 3591068 A1 | 1/2020 |
| EP | 2970668 B1 | 7/2020 |
| EP | 3782722 A1 | 2/2021 |
| EP | 3417941 B1 | 3/2022 |
| EP | 4219749 A2 | 8/2023 |
| EP | 4372100 A1 | 5/2024 |
| JP | 3568846 B2 | 9/2004 |
| WO | WO-2008079274 A1 | 7/2008 |
| WO | WO-2009149449 A1 | 12/2009 |
| WO | WO-2015097185 A1 | 7/2015 |
| WO | WO-2017210182 A1 | 12/2017 |
| WO | WO-2017215428 A1 | 12/2017 |
| WO | WO-2017215429 A1 | 12/2017 |
| WO | WO-2019226970 A1 | 11/2019 |
| WO | WO-2020001529 A1 | 1/2020 |
| WO | WO-2020010137 A1 | 1/2020 |
| WO | WO-2020037113 A1 | 2/2020 |
| WO | WO-2020037130 A1 | 2/2020 |
| WO | WO-2020055834 A2 | 3/2020 |
| WO | WO-2020078466 A1 | 4/2020 |
| WO | WO-2021037999 A2 | 3/2021 |
| WO | WO-2021119201 A1 | 6/2021 |
| WO | WO-2021119202 A1 | 6/2021 |
| WO | WO-2022187684 A1 | 9/2022 |
| WO | WO-2022256612 A1 | 12/2022 |
| WO | WO-2023034531 A1 | 3/2023 |
| WO | WO-2023122041 A1 | 6/2023 |
| WO | WO-2023133094 A1 | 7/2023 |
| WO | WO-2023172977 A1 | 9/2023 |
| WO | WO-2024054825 A1 | 3/2024 |

OTHER PUBLICATIONS

Chapman, H. Glenn et al.: Angular Domain Image Detectability with Changing Turbid Medium Scattering Coefficients. Proc. of SPIE 5695:160-171 (2005).

Digital polymerase chain reaction. Wikipedia, Sep. 18, 2024; [retrieved on Dec. 4, 2024]. Available at URL:https://en.wikipedia.org/w/index.php?title=Digital_polymerase_chain_reaction&oldid=979089524 pp. 1-17.

Engelbrecht, Christoph J et al.: Miniaturized selective plane illumination microscopy for high-contrast in vivo fluorescence imaging. Opt Lett. 35(9):1413-5 (2010). doi: 10.1364/OL.35.001413.

EP21787733.1 Extended European Search Report dated Apr. 25, 2024.

Evonik Industries. Abil WE 09, Emulsifier for the formulation of W/O creams and lotions. [Retrieved on Mar. 19, 2025]. Available at URL:https://glenncorp.com/wp-content/uploads/2013/11/DS_ABIL_WE_09_e.pdf pp. 1-5.

Extended European Search Report dated Jan. 2, 2025 issued in European Patent Application No. 22764175.0.

(56) References Cited

OTHER PUBLICATIONS

Heggazy, Marihan et al.: Proximity ligation assay for detecting protein-protein interactions and protein modifications in cells and tissues in situ. Current Protocols in Cell Biology 89(1): e115, 1-23 (2020).

Huang, Yanyi et al.: Centrifugal micro-channel array droplet generation for highly parallel digital PCR. Lap on a Chip 17(2):235-240 (2017).

Jiang, Hao et al.: Droplet-based light-sheet fluorescence microscopy for high-throughput sample preparation, 3-D imaging and quantitative analysis on a chip. Lab Chip 17(13):2193-2197 (2017).

Jiang, L. et al.: Digital antimicrobial susceptibility testing using the MilliDrop technology. European journal of clinical microbiology and infectious diseases 35(3):415-422 (2016).

Leong, TSH et al.: Minimising Oil Droplet Size Using Ultrasonic Emulsification. Ultrasonics Sonochemistry 16(6):721-727 (2009).

Liao et al.: Combination of fluorescence color and melting temperature as a two-dimensional label for homogeneous multiplex PCR detection. Nucleic Acids Research 2013, 41:7 e76 (2013).

Liao, Peiyu et al.: Lossless and Contamination-Free Digital PCR. bioRxiv : 1-15 (2019).

Liao, Peiyu et al.: Three-dimensional Digital PCR Through Light-sheet Imaging of Optically Cleared Emulsion. Editor David A. Weitz, Harvard University, Cambridge, MA, Applied Physical Sciences 117(41):25628-25633 (2020). https://doi.org/10.1073/pnas.2002448117.

McMahon et al.: Multiplexed Single Intact Cell Droplet Digital PCR (MuSIC ddPCR) Method for Specific Detection of Enterohemorrhagic *E. coli* (EHEC) in Food Enrichment Cultures. Frontiers in Microbiology 8:332 (2017).

PCT/CN2017/085891 International Search Report and Written Opinion dated Sep. 1, 2017.

PCT/CN2017/085892 International Search Report and Written Opinion dated Aug. 11, 2017.

PCT/CN2019/093241 International Search Report and Written Opinion dated Oct. 8, 2019.

PCT/CN2019/111938 International Search Report and Written Opinion dated Jan. 16, 2020.

PCT/US2021/027353 International Search Report and Written Opinion dated Aug. 13, 2021.

PCT/US2022/018994 (WO2022187684) International Search Report and Written Opinion dated Jun. 30, 2022.

Saghafi, Saiedeh et al.: Recent development in light Ultramicroscopy using aspherical optical elements. Proc. of SPIE 8550:85500K-1-85500K-6 (2012).

Saghafi; Saiedeh et al.: Recent development in light Ultramicroscopy using aspherical optical elements. SPIE Optical Systems Design, vol. 8550, 85500K (2012) (abstract).

Schulman et al.: Formation of microemulsions by amino alkyl alcohols. Ann N Y Acad Sci. 92:366-371 doi:10.1111/j.1749-6632.1961.tb44987.x (1961).

U.S. Appl. No. 17/230,910 Notice of Allowance dated Sep. 28, 2021.

U.S. Appl. No. 17/230,910 Office Action dated Jul. 23, 2021.

U.S. Appl. No. 17/255,409 Office Action dated Aug. 5, 2024.

U.S. Appl. No. 17/286,421 Office Action dated Mar. 24, 2025.

U.S. Appl. No. 17/687,080 Office Action dated Jul. 16, 2024.

U.S. Appl. No. 17/687,080 Office Action dated Mar. 14, 2024.

U.S. Appl. No. 17/711,417 Notice of Allowance dated Apr. 10, 2024.

U.S. Appl. No. 17/711,417 Notice of Allowance dated Feb. 21, 2024.

U.S. Appl. No. 17/711,417 Office Action dated Jul. 7, 2023.

U.S. Appl. No. 17/985,485 Office Action dated Sep. 16, 2025.

U.S. Appl. No. 18/646,572 Supplemental Notice of Allowability dated Jan. 27, 2025.

U.S. Appl. No. 18/646,572 Supplemental Notice of Allowability dated Jan. 31, 2025.

U.S. Appl. No. 18/948,248 Notice of Allowance dated Jan. 2, 2025.

U.S. Appl. No. 18/948,248 Supplemental Notice of Allowability dated Feb. 12, 2025.

U.S. Appl. No. 19/063,118 Corrected Notice of Allowability dated Oct. 23, 2025.

U.S. Appl. No. 19/063,118 Notice of Allowance dated Aug. 29, 2025.

U.S. Appl. No. 19/063,118 Notice of Allowance dated Dec. 17, 2025.

U.S. Appl. No. 19/063,118 Office Action dated May 8, 2025.

Vladisavljević et al.: Production of uniform droplets using membrane, microchannel and microfluidic emulsification devices. Microfluidics and Nanofluidics 13:151-178 (2012).

Warren, Luigi et al.: Transcription factor profiling in individual hematopoietic progenitors by digital RT-PCR. PNAS 103(47):17807-17812 (2006). www.pnas.org/cgi/doi/10.1073/pnas.0608512103.

Wright et al.: The use of cell-free fetal nucleic acids in maternal blood for non-invasive prenatal diagnosis. Human Reproduction Update 15(1):139-151 (2009).

Yamashita et al.: Generation of monodisperse cell-sized microdroplets using a centrifuge-based axisymmetric co-flowing microfluidic device. J. Biosci Bioeng 119(4):492-495 (2015). https://www.sciencedirect.com/science/article/pii/S1389172314003545.

Yamashita et al.: Generation of monodisperse cell-sized microdroplets using a centrifuge-based axisymmetric co-flowing microfluidic device. Journal of Bioscience and Bioengineering 119(4): 492-495 (2014).

Yanny et al.: Miniscope3D: optimized single-shot miniature 3D fluorescence microscopy. Light: Science & Applications 9:171 (2020).

Zhao et al.: Massive droplet generation for digital PCR via a smart step emulsification chip integrated in a reaction tub. Analyst 2021, 146:15568 (2021).

Zhao, Yongxi et al.: Isothermal Amplification of Nucleic Acids. Chemical Reviews 115(22):12491-12545 (2015).

Zhu et al., Highly sensitive and quantitative detection of rare pathogens through agarose droplet microfluidic emulsion PCR at the single-cell level. Lab On a Chip 12(20):3907-3913 (2012).

Aspiration/
Delivery
(e.g., pipette tip)

Reservoir Inlet
115

Sealing Body 130

Reservoir
Outlet
116

Receiving
Container
150

Reservoir 114e

1st Substrate 110e

Membrane 120e

Assembled

Disssembled

2nd Substrate 160e

Collecting Container 150e

Assembled Cross-Section

Supporting Body 170e (e.g., Centrifuge Swing Bucket)

Membrane 120f

2nd Substrate (spacer) 160f

Collecting Container 150f

Spacer 160f
Gap
Base Surface 50f

Assembled Cross-Section

Non-spacer
No Gap
Base Surface 50f

Assembled Cross-Section

EXAMPLE COLLECTING CONTAINER FORMATS
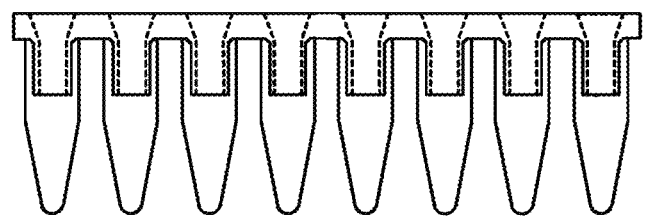
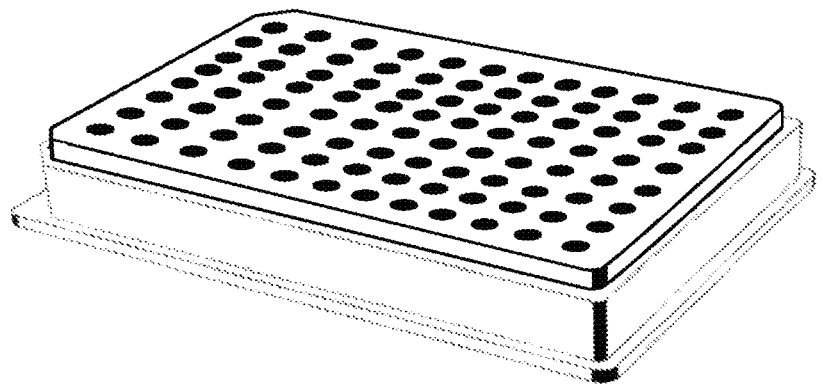
FIG. 7C

Method 200

generating a plurality of droplets within a collecting container at a high rate, each of the plurality of droplets including an aqueous mixture for a digital analysis S210

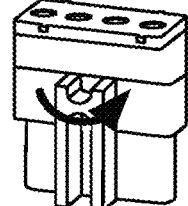

Stabilizing the plurality of droplets in position in a close-packed format within a continuous phase, within a region of the collecting container S220 transmitting heat to and from the plurality of droplets, within the collecting container, during a heat transmission operation S230

Performing an optical interrogation operation with the plurality of droplets within the collecting container S240

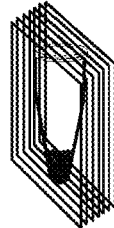

FIG. 8

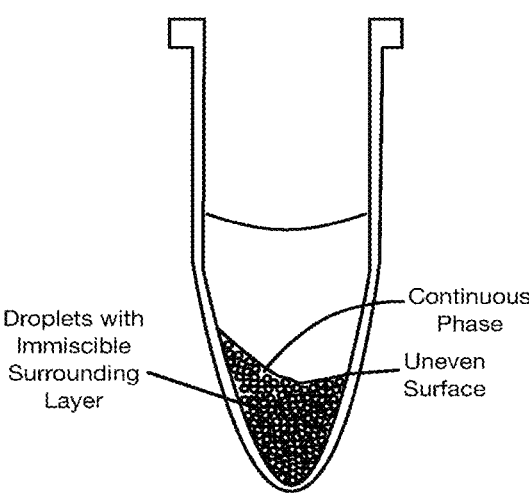
Droplets with Immiscible Surrounding Layer
Continuous Phase
Uneven Surface
FIG. 9A
spinning in a first direction
of rotation,
and reversing the direction
of rotation
S214
Even Surface
FIG. 9B
spinning at a
first rotational velocity
and at a
second rotational velocity
S216
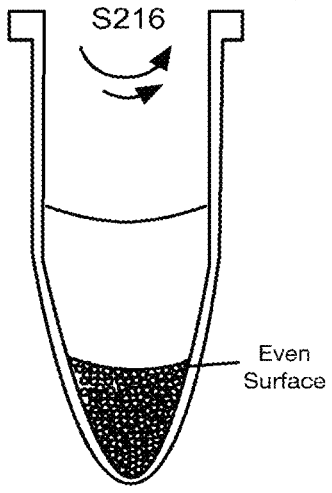
Even Surface
FIG. 9C Method 300 providing an assembly including: a first substrate defining one or more reservoirs, a membrane layer including a distribution of holes positioned downstream of the one or more reservoirs, and optionally one or more fasteners configured to retain the assembly in position relative to one or more receiving containers containing a first fluid S310 receiving a second fluid into the one or more reservoirs, wherein the second fluid is intended for use in droplet formation and is immiscible with the first fluid S320 applying force to contents of the reservoirs/assembly, thereby driving the second fluid from the one or more reservoirs, through the membrane layer, and into the one or more receiving containers S330

FIG. 10

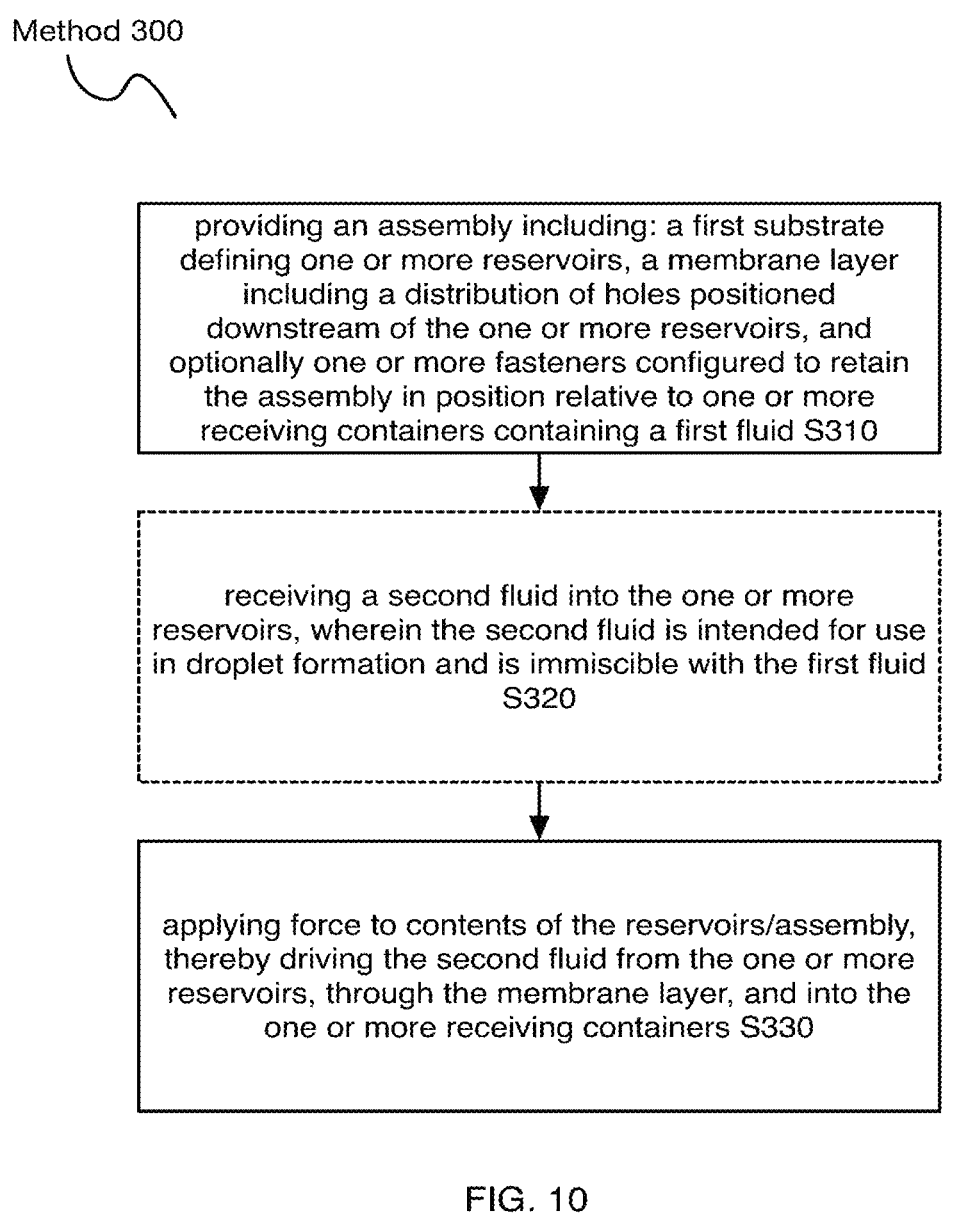

SYSTEMS AND METHODS FOR GENERATING DROPLETS AND PERFORMING DIGITAL ANALYSES

CROSS-REFERENCE

This application is a continuation of U.S. patent application Ser. No. 19/063,118, filed Feb. 25, 2025, which is a continuation application of U.S. patent application Ser. No. 18/948,248, filed Nov. 14, 2024, now U.S. Pat. No. 12,270, 815, issued Apr. 8, 2025, which is a continuation application of U.S. patent application Ser. No. 18/646,572, filed Apr. 25, 2024, now U.S. Pat. No. 12,265,088, issued Apr. 1, 2025, which is a continuation application of U.S. patent application Ser. No. 17/711,417, filed Apr. 1, 2022, now U.S. Pat. No. 12,000,842, issued Jun. 4, 2024, which is a continuation of PCT Patent Application number PCT/US2022/018994, filed Mar. 4, 2022, which claims the benefit of U.S. Provisional Application No. 63/157,292, filed Mar. 5, 2021, each of which is incorporated in its entirety herein by this reference.

TECHNICAL FIELD

This disclosure relates generally to fields related to sample processing and digital analyses, and more specifically to a new and useful systems and methods for generation of and digital analysis of partitions in such fields.

BACKGROUND OF THE INVENTION

In biotechnology and other applications, partitioning technologies play a significant role in achieving the ability to conduct microscale and nanoscale analyses (e.g., of single cells, of single molecules, of other analytes, etc.). Dispersing samples across partitions in a consistent and reliable manner has utility in relation to various assays in cell and molecular biology, with respect to digital analyses (e.g., digital polymerase chain reaction) and other bioassays. Isolated and independent reaction environments provided in a partitioned-format can further greatly reduce the sample and process fluid volume required, reducing costs associated with sample processing. Results returned from such assays can be used for clinical and non-clinical characterizations of various conditions.

SUMMARY OF THE INVENTION

Currently, methods and systems for distributing samples across partitions in a rapid and consistent manner, in a manner where partition contents are stably isolated without leakage or merging of contents of adjacent partitions, and in a manner that enables readout from signals from the partitions, are severely limited. Commercially available platforms conduct partitioning by using microfluidic devices involving complex setups. However, such platforms may be costly, partition samples at a slow rate, are labor-intensive, or can cause sample contamination. Thus, there is a need in the field of sample processing to create new and useful systems and methods for generation of and digital analysis of partitions.

Accordingly, this disclosure describes embodiments, variations, and examples of systems, methods and compositions for rapid partitioning of samples for digital analyses.

An aspect of the disclosure provides embodiments, variations, and examples of a device for rapidly generating partitions (e.g., droplets from a sample fluid, droplets of an emulsion), wherein, the device includes: a first substrate defining a reservoir comprising a reservoir inlet and a reservoir outlet; a membrane coupled to the reservoir outlet and comprising a distribution of holes; and a supporting body comprising an opening configured to retain a collecting container in alignment with the reservoir outlet. During operation, the first substrate can be coupled with the supporting body and enclose the collecting container, with the reservoir outlet aligned with and/or seated within the collecting container. During operation, the reservoir can contain a sample fluid, where application of a force to the device or sample fluid generates a plurality of droplets within the collecting container at an extremely high rate (e.g., of at least 200,000 droplets/minute, of at least 300,000 droplets/minute, of at least 400, droplets/minute, of at least 500,000 droplets/minute, of at least 600,000 droplets/minute, of at least 700,000 droplets/minute, of at least 800,000 droplets/minute, of at least 900,000 droplets/minute, of at least 1 million droplets/minute, of at least 2 million droplets/minute, of at least 3 million droplets/minute, etc.), where the droplets are stabilized in position (e.g., in a close-packed format, in equilibrium stationary positions) within the collecting container. Notably, the droplets are stable across a wide range of temperatures (e.g., 1° C. through 95° C., greater than 95° C., less than 1° C.) relevant to various digital analyses and other bioassays, where the droplets remain consistent in morphology and remain unmerged with adjacent droplets.

In embodiments, variations, and examples, the membrane includes a distribution of holes having low density (e.g., significantly lower than that typical for filtration applications involving porous membranes).

In embodiments, variations, and examples, the device can include a set of reservoirs (e.g., at the first substrate), a set of membranes at outlets of the set of reservoirs, and a supporting body for a set of collecting containers, in order to provide parallel processing of multiple samples and/or combination of sample processing materials during the partitioning process.

In embodiments, variations, and examples, the device can include a spacer configured to separate the membrane(s) further from base surfaces or liquid interfaces within the collecting container(s), thereby enabling operation modes in which droplets emerging from the membrane pass through air or another initial fluid phase prior to arriving at respective equilibrium positions.

An aspect of the disclosure provides embodiments, variations, and examples of a method for rapidly generating partitions (e.g., droplets from a sample fluid, droplets of an emulsion) within a collecting container at an extremely high rate, each of the plurality of droplets including an aqueous mixture for a digital analysis (e.g., of nucleic acid material, of protein material, of amino acid material, of other analytes described), wherein upon generation, the plurality of droplets is stabilized in position (e.g., in a close-packed format, at equilibrium stationary positions, etc.) within a continuous phase (e.g., as an emulsion having a bulk morphology defined by the collecting container). In aspects, partition generation can be executed by driving the sample fluid through a distribution of holes of a membrane, where the applied force can be one or more of centrifugal, associated with applied pressure, magnetic, or otherwise physically applied.

In embodiments, variations, and examples, droplets generated can form an emulsion, with individual droplets isolated and stabilized in position within a collecting container. The emulsion can be a viscous fluid, a shear-thickening fluid, a gel (e.g., a gel having individual discrete droplets), or another fluid having a surface. When droplet generation is performed by way of centrifugation according to variations of the method(s) described, driving the sample fluid through the membrane can include spinning the sample fluid, the membrane, and the collecting container in a first direction of rotation, and reversing the direction of rotation, thereby adjusting a surface profile of an emulsion comprising the plurality of droplets within the collecting container. In relation to digital analyses involving optical interrogation of sections of the emulsion, adjusting the surface profile (e.g., by producing a more even/level/planar surface during centrifugation) can improve readout of signals proximal to all surfaces of the emulsion.

When droplet generation is performed by way of centrifugation according to variations of the method(s) described, driving the sample fluid through the membrane can include. spinning the sample fluid, the membrane, and the collecting container within a centrifuge at a first rotational velocity and at a second rotational velocity less than the first rotational velocity, thereby adjusting a surface profile of an emulsion comprising the plurality of droplets within the collecting container. In relation to digital analyses involving optical interrogation of sections of the emulsion, adjusting the surface profile (e.g., by producing a more even/level/planar surface during centrifugation) can improve readout of signals proximal to all surfaces of the emulsion.

In relation to a single-tube workflow in which the collecting container remains closed (e.g., the collecting container has no outlet, there is no flow out of the collecting container, to avoid sample contamination), method(s) can further include transmitting heat to and from the plurality of droplets within the closed collecting container according to an assay protocol. In relation to generation of emulsions having suitable clarity (e.g., with or without refractive index matching), method(s) can further include transmission of signals from individual droplets from within the closed collecting container, for readout (e.g., by an optical detection platform, by another suitable detection platform).

Where method(s) include transmitting heat to and from the plurality of droplets, within the closed container, the droplets are stable across a wide range of temperatures (e.g., 1° C. through 95° C., greater than 95° C., less than 1° C.) relevant to various digital analyses and other bioassays, where the droplets remain consistent in morphology and remain unmerged with adjacent droplets.

Examples of partition generation methods can include generating an extremely high number of droplets (e.g., greater than 2 million droplets, greater than 3 million droplets, greater than 4 million droplets, greater than 5 million droplets, greater than 6 million droplets, greater than 7 million droplets, greater than 8 million droplets, greater than 9 million droplets, greater than 10 million droplets, greater than 15 million droplets, greater than 20 million droplets, greater than 25 million droplets, greater than 30 million droplets, greater than 40 million droplets, greater than 50 million droplets, greater than 100 million droplets, etc.) within a collecting container having a volumetric capacity (e.g., less than 50 microliters, from 50 through 100 microliters and greater, etc.), where droplets have a characteristic dimension (e.g., from 1-50 micrometers, from 10-30 micrometers, etc.) that is relevant for digital analyses, single cell capture, target detection, individual molecule partitioning, to other applications.

The disclosure provides for systems, devices, and methods that enable digital analyses across a wide dynamic range that is 10-100 times greater than that of existing technologies, depending upon application of use. In examples related to nucleic acid counting, the disclosure provides for systems, devices, and methods that can have a dynamic range from 1 through 100 million, due to the extremely high number of uniform partitions generated from which signals can be read, and due to the ability to partition with low occupancy (e.g., less than 20% occupancy, less than 10% occupancy, less than 9% occupancy, less than 8% occupancy, less than 7% occupancy, less than 6% occupancy, less than 5% occupancy, etc.) of partitions by targets.

In specific applications, partitioning devices and methods described can perform: detection and counting of nucleic acid molecules via amplification of individual nucleic acid molecule captured within a droplet followed by detection of optically detectable signals (e.g., amplification by polymerase chain reaction (PCR) methods, by isothermal methods such as loop-mediated isothermal amplification (LAMP), by recombinase polymerase amplification (RPA), by helicase dependent amplification (HDA), by strand displacement amplification (SDA), by nicking enzyme amplification (NEAR), by transcription mediated amplification (TMA), by RNaseH mediated amplification, by whole genome amplification (WGA) using phi29, by rolling circle amplification, etc.) on purified DNA, cDNA, RNA, oligonucleotide tagged antibodies/proteins/small molecules, or directly from lysate (e.g., blood lysate); fluorescent in situ hybridization (FISH) with fluorescently tagged nucleic acids (e.g., PNA, LNA, DNA, RNA, etc.) or an indirect in situ hybridization approach using DIG or biotin, where the signal is later amplified by conjugation of an antibody to alkaline phosphatase or a peroxidase to produce a change in color detected by one or more substrates (e.g., nitroblue tetrazolium (NBT), 5-bromo-4-chloro-3-indolyl-phosphate (BCIP), HNPP, etc.); an in vitro transcription or translation assay whereby a colorimetric or fluorescent reporter is used for detection; droplet PCR applied to samples derived from single cells (e.g., prokaryotes, eukaryotes), organelles, viral particles, and exosomes; enumeration of protein or peptide molecules (e.g., by proximity ligation assays, etc.); sequencing applications (e.g., single molecule sequencing applications); monitoring or detection of products (e.g., proteins, chemicals) released from single cells (e.g., interleukin released from immune cells); monitoring cell survival and/or division for single cells; monitoring or detection of enzymatic reactions involving single cells; antibiotic resistance screening for single bacteria; enumeration of pathogens in a sample (e.g., in relation to infections, sepsis, in relation to environmental and food samples, etc.); enumeration of heterogeneous cell populations in a sample; enumeration of individual cells or viral particles (e.g., by encapsulating cells in droplets with species-specific antibodies coupled with enzymes that react with substrate components in the droplet to produce signals, etc.); monitoring of viral infections of a single host cell; liquid biopsies and companion diagnostics; prenatal diagnosis of genetic disorders (e.g., aneuploidy, genetically inherited diseases) such as with cell-free nucleic acids, fetal cells, or samples containing mixtures of fetal and maternal cells; detection of cancer forms from various biological samples (e.g., detection of cancer from cell-free nucleic acids, tissue biopsies, biological fluids, feces); detection and/or monitoring of minimal residual diseases; monitoring responses to therapies; detection or prediction of rejection events of transplanted organs; other diagnostics associated with other health conditions; other characterizations of statuses of other organisms; and other suitable applications.

In specific applications, the systems and methods for partitioning in a single tube workflow can perform emulsion digital PCR-associated processes.

In embodiments, the target material analyzed according to digital analysis and/or other bioassay techniques can include one or more of: nucleic acid material (e.g., DNA, RNA, miRNA, etc.), protein material, amino acid material, other small molecules, other single analytes, other multi-analytes, and/or other suitable target material of a sample. In embodiments, the sample can include or otherwise be derived from whole tissue structures, tissue portions (e.g., histological tissue slices, formalin-fixed paraffin-embedded (FFPE) tissue, frozen tissue, biopsied tissues, fresh frozen plasma, seeded natural scaffolds, seeded synthetic scaffolds, etc.), organs, whole organisms, organoids, cell suspensions (e.g., frozen cell suspensions that are separated prior to processing with the system, cell suspensions retained in a medium/ hydrogel medium, etc.), nuclei suspension, single cells, organelles, sub-organelle structures, intra-organelle components, viruses, microorganisms, and other samples.

An additional aspect of the present disclosure provides for a method comprising: generating a plurality of droplets within a collecting container at a rate of at least 1 million droplets per minute, each of the plurality of droplets comprising an aqueous mixture for a digital analysis of nucleic acid material.

In some embodiments, upon generation, the plurality of droplets is stabilized in position in a close-packed format within a continuous phase, within a region of the collecting container. In some embodiments, generating the plurality of droplets comprises driving a sample fluid through a membrane comprising a distribution of holes, the membrane coupled to a reservoir outlet of a reservoir for the sample fluid, and the reservoir aligned with the collecting container. In some embodiments, the distribution of holes has a density less than 5000 holes per cm$^2$ and a hole-to-hole spacing greater than 30 micrometers. In some embodiments, each hole in the distribution of holes has a diameter from 1 through 3 micrometers. In some embodiments, driving the sample fluid through the membrane comprises spinning the sample fluid, the membrane, and the collecting container within a centrifuge in a first direction of rotation, and reversing the direction of rotation, thereby adjusting an equilibrium surface profile of an emulsion comprising the plurality of droplets within the collecting container. In some embodiments, driving the sample fluid through the membrane comprises spinning the sample fluid, the membrane, and the collecting container within a centrifuge at a first rotational velocity and at a second rotational velocity less than the first rotational velocity, thereby adjusting an equilibrium surface profile of an emulsion comprising the plurality of droplets within the collecting container. In some embodiments, the collecting container has a volumetric capacity from 10 through 300 microliters, and wherein each of the plurality of droplets has a characteristic diameter from 10 through 30 micrometers. In some embodiments, the method further comprises transmitting heat to and from the plurality of droplets, within the collecting container, during a heat transmission operation, wherein the temperature varies within a temperature range from 4° C. to 95° C. during the heat transmission operation, and wherein individual droplets of the plurality of droplets remain unmerged with adjacent droplets in a close-packed format during the heat transmission operation. In some embodiments, generating the plurality of droplets comprises generating greater than 25 million droplets within the collecting container. In some embodiments, generating the plurality of droplets comprises transmitting two dimensional arrays of droplets toward a closed end of the collecting container, thereby stabilizing the plurality of droplets in a three dimensional close-packed format toward the closed end of the collecting container.

An additional aspect of the present disclosure provides for a system for generating droplets, the system comprising: a first substrate defining a reservoir comprising a reservoir inlet and a reservoir outlet; a membrane coupled to the reservoir outlet and comprising a distribution of holes; and a second substrate comprising an opening configured to retain a collecting container in alignment with the reservoir outlet, wherein the system comprises: a first operation mode wherein the first substrate is coupled with the second substrate and encloses the collecting container, with the reservoir outlet seated within the collecting container, a second operation mode wherein the reservoir contains a sample fluid comprising an aqueous mixture for a digital analysis of nucleic acid material, and a third operation mode wherein the membrane generates a plurality of droplets within the collecting container at a rate of at least 1 million droplets per minute in response to a force applied to the sample fluid, and a fourth operation mode wherein the plurality of droplets is stabilized in position in a close-packed format within a region of the collecting container.

In some embodiments, the membrane is bonded to the reservoir outlet at a perimeter of the reservoir outlet. In some embodiments, the distribution of holes has a density less than 10,000 holes per cm$^2$ and a hole-to-hole spacing greater than 10 micrometers. In some embodiments, the first substrate comprises a set of reservoirs comprising the reservoir; and the system further comprises a set of membranes comprising the membrane, the set of membranes paired with and bonded to outlets of the set of reservoirs; and the second substrate comprises a set of openings comprising the opening, wherein the set of openings is configured to retain a set of collecting containers in alignment with the set of reservoirs. In some embodiments, a reservoir number of the set of reservoirs is different from a collecting container number of the set of collecting containers, wherein the first substrate comprises two or more fluidic pathways from the set of reservoirs to the set of membranes. In some embodiments, the second substrate is configured as a spacer separating the reservoir outlet from a base surface of the collecting container.

An additional aspect of the present disclosure provides for a method comprising: generating a plurality of droplets within a collecting container, each of the plurality of droplets comprising an aqueous mixture for a digital analysis of nucleic acid material, wherein generating the plurality of droplets comprises driving the aqueous mixture through a distribution of holes of a track-etched membrane to stabilized positions, toward a closed end of the collecting container, and wherein the plurality of droplets is characterized by less than 13% coefficient of variation for polydispersity.

In some embodiments, generating the plurality of droplets comprises generating the plurality of droplets at a rate of at least 600,000 droplets per minute. In some embodiments, the plurality of droplets is characterized by less than 10% occupancy of droplets by said nucleic acid material. Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. The present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference in their entireties for all purposes and to the same extent as if each individual publication, patent, or patent application was specifically and individually indicated to be incorporated by reference.

Furthermore, where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

BRIEF DESCRIPTION OF THE DRAWINGS

FIG. 7C depicts examples of collecting containers of a system for generating droplets.

FIG. 8 depicts a flow chart of an embodiment of a method for generating droplets.

FIGS. 9A-9C depict examples of methods for producing desired surface characteristics of emulsions generated according to methods described.

FIG. 10 depicts a flow chart of an embodiment of a method for generating droplets.

DETAILED DESCRIPTION OF THE INVENTION(S)

Figure 1:
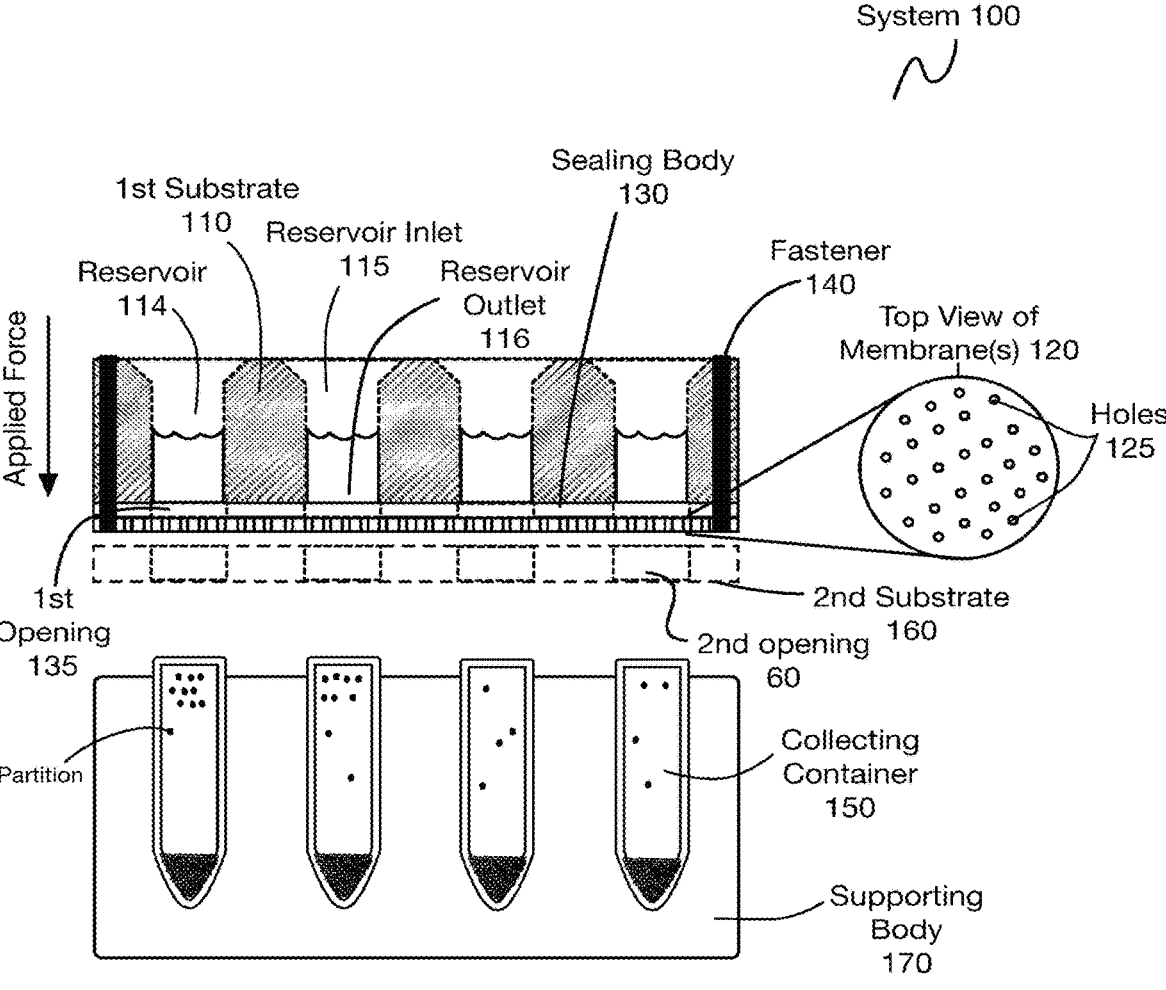
FIG. 1 depicts an embodiment of a system for generating droplets.

While various embodiments of the invention have been shown and described herein, it will be obvious to those skilled in the art that such embodiments are provided by way of example only. Numerous variations, changes, and substitutions can occur to those skilled in the art without departing from the invention. It should be understood that various alternatives to the embodiments of the invention described herein can be employed.

1. General Overview

The present disclosure covers systems, devices, methods performed by such systems and devices, and methods of manufacturing and assembling such devices. Generally, embodiments of the device include assemblies of reservoirs, functionalized membranes, and supporting bodies for collecting containers, where the assemblies rapidly produce droplets of an emulsion for digital analyses or other applications of use. Droplets produced by such devices are stabilized in a three dimensional format within closed collecting containers, thereby providing a "single-tube" workflow that eliminates risk of sample cross-contamination from initial reception of a sample, to distributing of the sample across an extremely high number of partitions, to performance of reactions within individual partitions, to detecting signals generated by contents of individual partitions from with the closed collecting containers.

The systems, methods, and devices disclosed herein can provide several additional benefits over other systems and methods, and such systems, methods, and devices are further implemented into many practical applications across various disciplines.

Devices, methods, and systems of the present disclosure may generate a plurality of droplets at an extremely high rate, where the droplets are stabilized in position (e.g., in a close-packed format, in equilibrium stationary positions) within a collecting container. Notably, the droplets are stable across a wide range of temperatures (e.g., 1° C. through 95° C., greater than 95° C., less than 1° C.) relevant to various digital analyses and other bioassays, where the droplets remain consistent in morphology and remain unmerged with adjacent droplets. Stabilization of the droplets within a continuous phase of an emulsion is further performed in a manner where the emulsion has a high degree of clarity (e.g., greater than 50% transmissivity of light, greater than 60% transmissivity of light, greater than 70% transmissivity of light, greater than 80% transmissivity of light, greater than 90% transmissivity of light, greater than 99% transmissivity of light, etc.), such that signals from cross-sections of the emulsion within the collecting container can be interrogated (e.g., using a 3D imaging technique, using a planar imaging technique, etc.).

The devices, systems, and methods disclosed herein can further generate droplets in a consistent and controlled manner (e.g., as monodisperse, uniform droplets with a low degree of polydispersity) for applications in biotechnology (e.g., with respect to microscale and nanoscale assays) to other fields.

The devices, systems, and methods disclosed herein further provide a cost-effective alternative to droplet generation using microfluidic devices, in a manner that generates droplets in a consistent and reliable manner. In specific examples, the systems and devices may include assemblies with track-etched membranes for producing droplets in a consistent and controlled manner (e.g., as monodisperse/uniform droplets). In these examples, hole density and/or hole-to-hole spacing of the membranes is significantly lower than that which may used for membrane-based filtration.

The present disclosure also provides disposable devices and methods for generating droplets using a single-tube and closed tube workflow from droplet generation through reaction performance within individual droplets, through optical interrogation of droplet contents, thereby preventing sample cross contamination throughout digital analyses processes.

Additionally or alternatively, in variations, the devices, methods, and systems disclosed herein can be adapted for transmitting an extremely high number of droplets, where the droplets are generated at an extremely high rate, to various well formats and tube formats, thereby improving performance of existing droplet-based systems.

In examples, the systems, methods, and devices of the present disclosure have applications in digital amplification of nucleic acid molecules (e.g., digital polymerase chain reaction (PCR), digital loop-mediated isothermal amplification (LAMP), digital multiple displacement amplification (MDA), digital recombinase polymerase amplification (RPA), digital helicase dependent amplification, reverse transcription, in vitro transcription and translation, overlap extension amplification, etc.).

In examples, the systems, methods, and devices of the present disclosure have applications in single cell and organelle capture (e.g., for mammalian cells, for bacterial cells, for pathogens, for viral particles, for organelles, etc.).

In examples, the systems, methods, and devices of the present disclosure have applications in single, double, or other emulsion generation. For instance, the systems, methods, and devices disclosed herein can use one or more of centrifugation, pressure, or other forces to disperse a fluid, as droplets, through one or more layers of fluids (i.e., 'continuous fluids') that are immiscible with each other, forming emulsions.

In examples, the systems, methods, and devices of the present disclosure can have applications in microparticle generation and liposome generation for other applications.

Additionally or alternatively, the systems, devices, or methods described can confer any other suitable benefit.

2. Systems

As shown in FIG. 1, an embodiment of a system 100 for generation of droplets includes: a first substrate 110 defining a set of reservoirs 114, each having a reservoir inlet 115 and a reservoir outlet 116; one or more membranes 120 positioned adjacent to reservoir outlets of the set of reservoirs 114, each of the one or more membranes 120 including a distribution of holes 125; and optionally, a sealing body 130 positioned adjacent to the one or more membranes 120 and including a set of openings 135 aligned with the set of reservoirs 114; and optionally, one or more fasteners (including fastener 140 shown in FIG. 1) configured to retain the first substrate 110, the one or more membranes 120, and optional the sealing body 130 in position relative to a set of collecting containers 150. In variations, the system 100 can additionally include a second substrate 160, wherein the one or more membranes 120 and optionally, the sealing body 130, are retained in position between the first substrate 110 and the second substrate 160 by the one or more fasteners.

Embodiments of the system 100 function to generate a plurality of droplets at an extremely high rate (e.g., of at least 200,000 droplets/minute, of at least 300,000 droplets/minute, of at least 400, droplets/minute, of at least 500,000 droplets/minute, of at least 600,000 droplets/minute, of at least 700,000 droplets/minute, of at least 800,000 droplets/minute, of at least 900,000 droplets/minute, of at least 1 million droplets/minute, of at least 2 million droplets/minute, of at least 3 million droplets/minute, etc.), where the droplets are stabilized in position (e.g., in a close-packed format, in equilibrium stationary positions) within a collecting container. Rates of droplet generation can be average rates determined in relation to duration of applied force.

Embodiments of the system may further function to reliably generate droplets in a consistent and controlled manner (e.g., as monodisperse and uniform droplets having little-to-no polydispersity) for various applications, such as digital amplification and analysis and other assays; capture of target material at cellular, subcellular, and molecular scales; sample analysis benefitting from droplet generation; or other suitable applications. Embodiments of the system 100 also function to generate droplets using devices that are non-microfluidic, disposable or reusable, in a cost-effective manner.

Embodiments of the system 100 can be used to implement one or more steps of methods described in Section 3 below. However, the system 100 can additionally or alternatively be configured to perform other suitable methods.

2.1 System—Supporting Substrates/Housing 2.1.1 Supporting Substrates—First Substrate FIG. 1 depicts an embodiment of a system 100, where the system 100 includes a first substrate 110 defining a set of reservoirs 114, each having a reservoir inlet 115 and a reservoir outlet 116. The first substrate 110 can function to provide at least a portion of a coupling mechanism for retaining positions of other elements of the system 100 relative to one or more collecting containers 150 described in more detail below. The first substrate 110 also functions to receive and stage fluid to be transmitted through the membrane layer 120 for formation of droplets. The first substrate 110 can be configured to disposable (e.g., composed of inexpensive, recyclable, and/or compostable materials), such that the system 100 can provide a cost-effective alternative for generation of droplets. Additionally or alternatively, the first substrate 110 can be configured to be a reusable element (e.g., usable for generation of droplets in multiple runs of the system 100).

In order to provide a robust mechanism of coupling with other system elements (e.g., supporting bodies for the collecting containers 150, a second substrate 160 described below, etc.), the first substrate 110 can be composed of a material having suitable mechanical properties. In variations, materials of the first substrate 110 can be configured to provide suitable mechanical properties in relation to stresses attributed to flow through set of reservoirs 114 (e.g., stresses due to centrifugation, stresses due to pressurization, radial stresses, shear stresses, longitudinal stresses, tensile stresses, compressive stresses, stresses associated with impacts to the system 100 during use; stresses due to thermal expansion, stresses due to thermal contraction, and other associated stresses depending upon applications of use).

Additionally or alternatively, the first substrate 110 can be composed of a material having suitable thermal properties. In variations, materials of the first substrate 110 can be configured to provide suitable thermal properties in relation to one or more of: thermal conductivity (e.g., in relation to heating or cooling of fluids from which droplets are generated by the system 100) and other thermal properties depending upon application of use.

Additionally or alternatively, the first substrate 110 can be composed of a material having suitable physical or surface properties. In variations, materials of the housing 121 and/or other aspects of the interface 120 can be configured to provide suitable physical or surface properties in relation to one or more of: non-reactiveness with sample materials; low porosity (e.g., so as to not absorb sample material); high hydrophobicity; and other suitable physical or surface properties.

Additionally or alternatively, the first substrate 110 can be composed of a material having suitable optical properties (e.g., for optical interrogation of sample materials, for protecting sample materials from electromagnetic radiation, etc.). In variations, the first substrate 110 is translucent, transparent, or otherwise has a high degree of transparency, to support optical interrogation of sample materials or sample processing materials within the set of reservoir(s) 114. Furthermore, translucent or transparent characteristics of the first substrate 110 may enable operation modes in which contents of the set of reservoirs 114 can be visualized (e.g., during manual filling, during automatic filling), such that a level of material within each reservoir can be verified prior to generation of partitions using the system 100. As such, the first substrate 110 can be composed of a material having a suitable level of transparency. Still alternatively, the first substrate 110 can be composed of an opaque material.

In variations, the first substrate 110 can be composted of a synthetic material or a natural material. In examples, the first substrate 110 can be composed of a polymeric material (e.g., a polyetheretherketone, an acetal, an acrylonitrile butadiene styrene, a nylon, a polycarbonate, a polypropylene, a polystyrene, etc.); a metallic material, a ceramic material, a composite material, or another suitable material. The first substrate 110 can be fabricated by machining, printing (e.g., 3D printing), molding (e.g., injection molding), or through another suitable method.

In variations, the first substrate 110 can have a broad surface at which access (e.g., through openings) into the set of reservoirs 114 is provided. As shown in FIG. 1, each reservoir can have a reservoir inlet 115 and a reservoir outlet 116. The reservoir inlet 115 can be defined as an open surface at the broad surface of the first substrate 110, and the reservoir outlet can be defined as an open surface at a second surface of the first substrate 110. Each reservoir can define a cavity for receiving fluid from which droplets are generated. In examples the cavity can have a volume from 1 μL through 100 mL; however, variations of the cavity can have another suitable volume. The cavity can be constant in cross section (e.g., transverse cross section) from the reservoir inlet 115 to the reservoir outlet 116. Alternatively, the cavity may not be constant in cross section from the reservoir inlet 115 to the reservoir outlet 116. For instance, a portion of the cavity near the reservoir inlet 115 can include morphology (e.g., flared morphology) configured to complement a fluid delivery device (e.g., a pipette tip), thereby facilitating fluid transfer to the system 100 for droplet generation. Additionally or alternatively, the cavity can define a non-straight or non-linear path from the reservoir inlet 115 to the reservoir outlet 116. Furthermore, in variations, a reservoir of the set of reservoirs 114 can have a reservoir inlet 115 at any other suitable surface of the first substrate 110, a reservoir outlet 116 at any other suitable outlet of the first substrate 110, or define another suitable fluid path from the reservoir inlet 115 to the reservoir outlet 116.

One or more filters can further be positioned within the set of reservoirs 114 and/or otherwise positioned upstream of the one or more membranes 120 described in further detail below, where the filter(s) can function to remove undesired material and prevent undesired material from entering droplets or disrupting droplet formation. In examples, the filter(s) can be structured to allow passage of targets (e.g., nucleic acids, proteins, cells, viral material, chemicals, analytes, etc.) from the sample(s) for distribution across the plurality of droplets, where such filter(s) can accordingly have suitable sizes, porosity, hydrophobicity, surface charge, and/or other characteristics.

Figure 2:
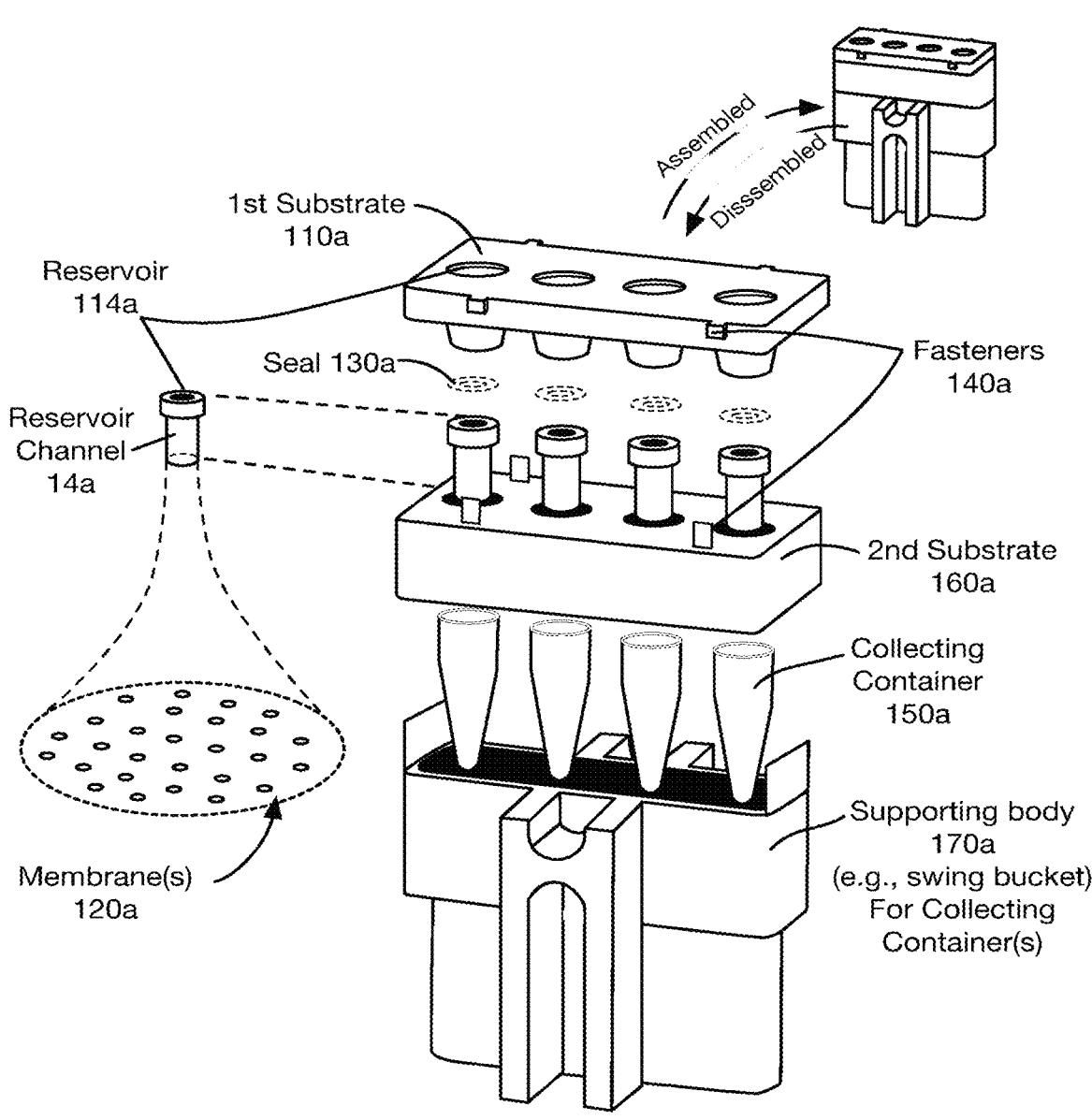
FIG. 2 depicts a first example of a system for generating droplets.

The example of the first substrate 110*a* shown in FIG. 2 includes four reservoirs corresponding to four collecting containers (e.g., of a complementary apparatus) for generated droplets; however, the first substrate 110 can alternatively define another suitable number of reservoirs (e.g., from one to 10000 reservoirs). Furthermore, the number of reservoirs may not correspond to the number of collecting containers in a one-to-one manner. For instance, the first substrate 110 can define a number of reservoir inlets fewer than that of the number of collecting containers, where the reservoirs can be configured to branch along their respective lengths and terminate at outlets corresponding to the collecting containers. As such, a number of samples can be distributed across a number of collecting containers, where the number of collecting containers is greater than the number of samples. Alternatively, the first substrate 110 can define a number of reservoir inlets greater than that of the number of collecting containers. As such, contents of multiple reservoirs can be combined prior to distribution across a set of collecting containers (e.g., in variations in which samples and processing materials are mixed within reservoirs prior to generation of droplets). As such, a reservoir number of the set of reservoirs can be different from a collecting container number of the set of collecting containers, and the first substrate can include one or more fluidic pathways (or two or more fluidic pathways) from the set of reservoirs to the set of membranes.

The first substrate 110 can include features configured to receive or position the set of fasteners 140 (described in more detail below) for coupling with other elements of the system 100, in order to enable retention of the elements of the system 100 in position relative to each other. Such features maintain alignment and relative positioning between system elements and provide proper sealing of elements (e.g., membranes to reservoir outlets). In the example shown in FIG. 2, the set of fasteners 140*a* can include a set of protrusions at the first substrate 110*a*, that complement tabs at the second substrate 160*a*.

Figure 3:
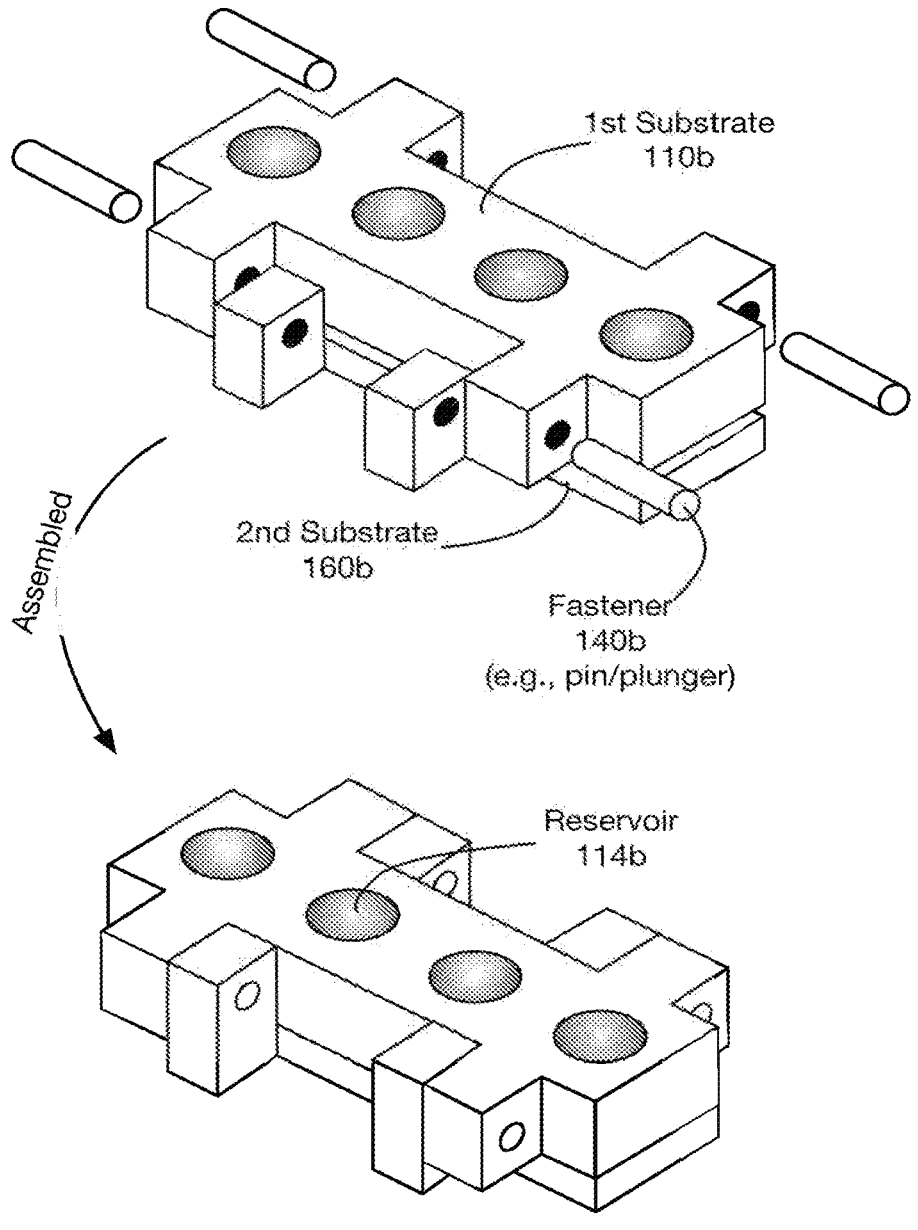
FIG. 3 depicts a variation of a fastener configuration in a system for generating droplets.

Alternatively, as shown in FIG. 3, the first substrate 110*c* can include a set of flanges defining through-holes through the flanges with an orientation parallel to the broad surface of the first substrate 110*b*, such that the set of fasteners including fastener 140*b* pass parallel to the broad surface through corresponding openings of a complementary element (e.g., second substrate 110*b*, collecting container supporting body, etc.). In this variation, separation of the first substrate 110 from the complementary element would apply shear to the set of fasteners.

Figure 4:
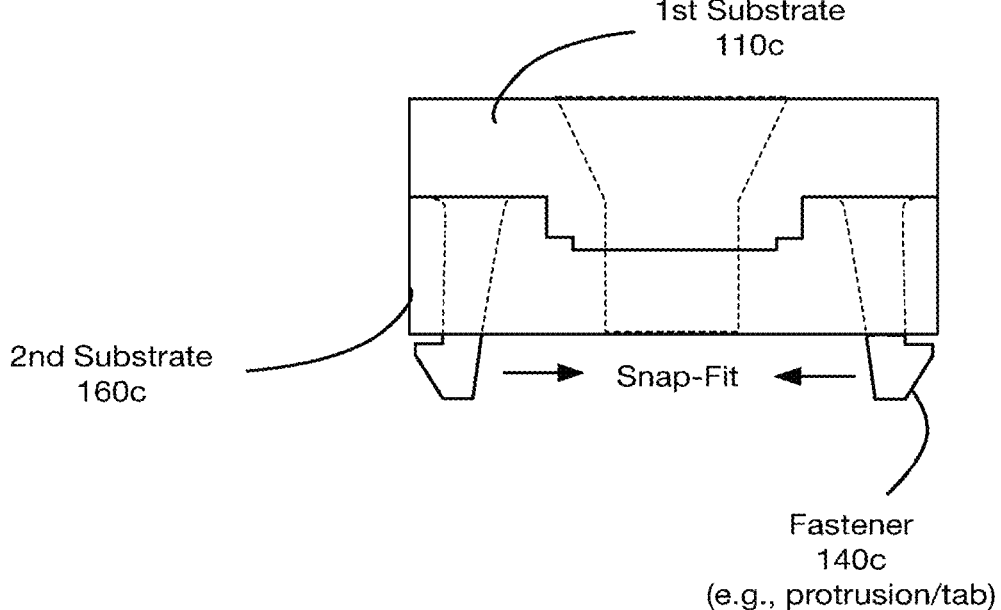
FIG. 4 depicts a variation of a fastener configuration in a system for generating droplets.

Still alternatively, the first substrate 110 may not define any openings or through holes, but enable fastening using another suitable mechanism. For instance, the first substrate 110 can include one or more of: protrusions (e.g., tabs, as shown in FIG. 4) that form a portion of a snap-fit mechanism between the first substrate 110*c* and recesses of a complementary element (e.g., second substrate 160*c*, collecting container supporting body, etc.); magnetic elements that enable magnetic coupling with a complementary element (e.g., second substrate 110, collecting container supporting body, etc.); adhesive elements that couple with a complementary element (e.g., second substrate 110, collecting container supporting body, etc.); and other suitable coupling mechanisms. The configurations shown in FIGS. 2, 3, and 4 provide reliable coupling between elements of the system

100, without providing obstacles to accessing the reservoir(s) of the first substrate.

Additionally or alternatively, the first substrate 110 can include features configured to receive or position the set of fasteners 140 for coupling to other elements of the system 100, in order to enable retention of the elements of the system 100 in position relative to each other. In one variation, the first substrate 110 can include a set of through holes passing perpendicular to the broad surface of the first substrate 110, in order to enable fastening between the first substrate 110 and a complementary element (e.g., second substrate 110, collecting container supporting body, etc.) with the membrane layer 120 and optionally, the sealing body 130 positioned (e.g., sandwiched, compressed) between the first substrate 110 and the complementary element. In this variation, separation of the first substrate 110 from the complementary element would apply tension to the set of fasteners 150.

2.1.2 Supporting Substrates—Second Substrate

In variations, the system 100 can additionally include a second substrate 160, wherein the one or more membranes 120 and optionally, the sealing body 130 are retained in position between the first substrate 110 and the second substrate 160 by the one or more fasteners 140 described in more detail below. In variations, the second substrate 160 can define openings (including second opening 60 shown in FIG. 1) corresponding to the set of reservoirs 114 and/or set of collecting containers 150, such that droplets formed upon transmission of fluid through the one or more membranes 120 pass through openings of the second substrate 160 and into the set of collecting containers 150. The openings of the second substrate 160 can further retain the collecting containers in position and/or in alignment with respective reservoir outlets, such that generated droplets are transferred directly into the collecting containers.

An example of the second substrate 160 is shown in FIG. 2, where the set of fasteners, including fastener 140a, couples the first substrate 110a to the second substrate 160, with the membranes 120a retained in position between the first substrate 110 and the second substrate 160. The second substrate 160a can be identical to or different from the first substrate 110 in material composition and/or properties described above. Furthermore, the second substrate 160a can include or define channels through which fluid passes into the collecting containers in a desired manner.

In the example shown in FIG. 2, the reservoir 114a is partially formed by the first substrate 110a and a reservoir channel 14a, where the reservoir channel 14a and the opening of the first substrate 110a cooperate to define a volume into which a material (e.g., sample fluid, process fluid, etc.), can be received for partitioning. As shown in FIG. 2, the first substrate 110a and the reservoir channel 14a can be sealed against each other (e.g., by a seal 130a, by using compliant materials, such that biasing the first substrate 110a against the reservoir channel 14a forms a seal, etc.). Furthermore, as shown in FIG. 2, the membrane 120a can be positioned at an outlet of the reservoir channel 14a and seated within the second substrate 160a, or pass through the second substrate into a respective collecting container 150a. In variations, the membrane 120a can be bonded to the reservoir outlet of the reservoir channel 14a, or retained in position in another manner (e.g., by being seated between the reservoir channel 14a and the second substrate 160a).

While embodiments, variations, and examples of the first substrate 110 described above include descriptions of a set of reservoirs, variations of the first substrate 110 and/or second substrate 160 can alternatively define a single reservoir or pathway into a single collecting container.

2.2 System—Membrane

As shown in FIG. 1, the system 100 may include one or more membranes 120 positioned adjacent to reservoir outlets of the set of reservoirs 114. The membrane layer 120 includes a distribution of holes 125, through which fluid from the set of reservoirs 114 passes or is driven to generate droplets for various applications. The one or more membranes 120 can further function to provide a cost-efficient alternative to microfluidic devices for generation of droplets, where the one or more membranes 120, along with other elements of the system 100 described, can generate droplets of a desired morphology (e.g., target droplet size in relation to sample volume and target total number of partitions) in a consistent (e.g., with high uniformity, with low merging, with low polydispersity) and reliable manner, and at an extremely rapid rate.

In relation to generation of droplets in a controlled manner, a membrane 120 of the system 100 can include or be composed of one or more track-etched membranes (e.g., membrane sheets) with precisely defined hole sizes, membrane thicknesses and hole densities. For generation of droplets, fluid in the one or more reservoirs upstream of the membrane layer 120 is forced through the distribution of holes 125 by way of applied forces (e.g., centrifugation, pressurized gas, etc.). The droplets formed upon exit of the distribution of holes 125 are then transmitted from the membrane 120 into one or more respective collecting containers described in more detail below, where the collecting containers contain a fluid (e.g., air, a fluid that is immiscible with the droplet material, etc.). While the membrane 120 can be track-etched to generate the distribution of holes in a precise manner (e.g., with respect to size, shape, and density), the membrane 120 can alternatively be generated without ion track techniques. For instance, the membrane 120 can alternatively be generated using another method (e.g., laser etching, chemical etching, electroporation, etc.).

As shown in FIG. 1, the one or more membranes 120 are configured to be retained in position adjacent to the reservoir outlets 116 of the first substrate 110. In variations, the membrane(s) 120 can thus be positioned within the reservoirs of the set of reservoirs 114 described above. Alternatively, the membrane layer 120 can be positioned outside of the reservoir outlets (e.g., at an external terminal portion of the reservoir 114, downstream of the reservoir outlets 116) of the first substrate 110.

In variations, the membrane(s) 120 can include a continuum of material positioned across all of the one or more reservoir outlets of the set of reservoirs, for instance, by sandwiching or otherwise retaining the membrane(s) 120 in position downstream of the reservoir outlets of the first substrate 110. Alternatively, the one or more membranes 120 can include separate bodies or regions of material positioned at terminal regions or within reservoirs of the first substrate 110. In variations wherein the one or more membranes 120 include separate bodies or regions of material, the separate bodies/regions can each have different characteristics (e.g., with respect to reservoirs carrying different types of fluids, with respect to generation of different size droplets, etc.). As such, in some variations, each reservoir can have its own associated membrane region that is separate from adjacent membrane regions. In variations where the one or more membranes 120 are divided, individual membrane regions can be divided by a physical barrier (e.g., a gap, a body of non-porous/non-absorbent material, etc.), or divided by another suitable barrier.

The one or more membranes 120 can be coupled to other adjacent system elements (e.g., the first substrate 110, reservoir outlets 116, optional sealing body 130, the second substrate 160, etc.) by one or more of: an adhesive, a thermal bond, mechanical bond, chemical bond, laser welding, ultrasonic welding, a light-cured adhesive, a temperature-cured adhesive, a moisture-cured adhesive, injection-molding (e.g., as a single piece using over-molding), and/or another suitable bonding mechanism.

Figure 5:
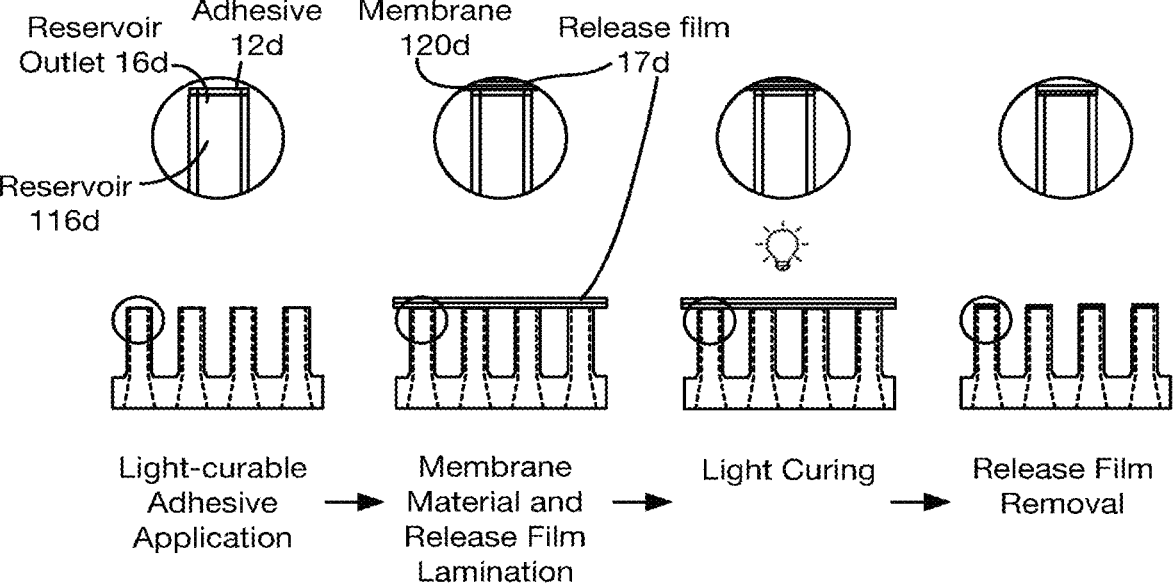
FIG. 5 depicts an example of a method for assembling components of a system for generating droplets.

FIG. 5 depicts an example method of bonding a membrane 120d to a reservoir outlet 16d of a reservoir 116d, at the perimeter of the reservoir outlet 116d. As shown in FIG. 5, light-curable (e.g., ultraviolet light-curable) adhesive 12d is applied to the perimeter of an exterior portion of the reservoir outlet 16d. Then, material of the membrane (e.g., track-etched polycarbonate, track-etched polyethylene, etc.) is applied to the reservoir outlet 16d at the perimeter, followed by application of a release film 17d over the material of the membrane 120d. The light-curable adhesive 12d is then exposed to light of appropriate wavelength(s) (e.g., ultraviolet light), followed by removal of the release film 17d and excess material of the membrane 120d. In variations, however, the membrane 120 can be coupled to the first substrate 110 and/or the reservoir 116 in another suitable manner.

In variations, the one or more membranes 120 can be composed of a polymeric material (e.g., polycarbonate, polyester, polyimide). In a first specific example, the one or more membranes 120 are polycarbonate track-etched (PCTE) membranes. In a second specific example, the one or more membranes 120 are polyethylene track-etched membranes. However, the one or more membranes 120 can alternatively be composed of another suitable material processed in another suitable manner.

In variations, the distribution of holes 120 can be generated in bulk membrane material with specified hole diameter(s), hole depth(s) (e.g., in relation to membrane thickness), aspect ratio(s), hole density, and hole orientation, where, in combination with fluid parameters, the structure of the membrane can achieve desired flow rate characteristics, with reduced or eliminated polydispersity and merging, and steady formation of droplets (e.g., without jetting of fluid from holes of the membrane).

In variations, the hole diameter can range from 0.2 micrometers to 30 micrometers, and in examples, the holes can have an average hole diameter can be 0.02 micrometers, 0.04 micrometers, 0.06 micrometers, 0.08 micrometers, 0.1 micrometers, 0.5 micrometers, 1 micrometers, 2 micrometers, 3 micrometers, 4 micrometers, 5 micrometers, 6 micrometers, 7 micrometers, 8 micrometers, 9 micrometers, 10 micrometers, 20 micrometers, 30 micrometers, any intermediate value, or greater than 30 micrometers (e.g., with use of membrane having a thickness greater than or otherwise contributing to a hole depth greater than 100 micrometers).

In variations, the hole depth can range from 1 micrometer to 200 micrometers (e.g., in relation to thickness of the membrane layer) or greater, and in examples the hole depth (e.g., as governed by membrane thickness) can be 1 micrometers, 5 micrometers, 10 micrometers, 20 micrometers, 30 micrometers, 40 micrometers, 50 micrometers, 60 micrometers, 70 micrometers, 80 micrometers, 90 micrometers, 100 micrometers, 125 micrometers, 150 micrometers, 175 micrometers, 200 micrometers, or any intermediate value.

In variations, the hole aspect ratio can range from 5:1 to 200:1, and in examples, the hole aspect ratio can be 5:1, 10:1, 20:1, 30:1, 40:1, 50:1, 60:1, 70:1, 80:1, 90:1, 100:1, 125:1, 150:1, 175:1, 200:1, or any intermediate value.

In variations, the hole density can range from 100 holes/$cm^2$ to 15000 holes/$cm^2$ (e.g., in order to prevent droplets generated from neighboring holes from merging together as they exit the holes, in relation to spin time, speed, and/or pressurization, etc.). In examples, the hole density can be 100 holes/$cm^2$, 200 holes/$cm^2$, 300 holes/$cm^2$, 400 holes/$cm^2$, 500 holes/$cm^2$, 600 holes/$cm^2$, 700 holes/$cm^2$, 800 holes/$cm^2$, 900 holes/$cm^2$, 1000 holes/$cm^2$, 2000 holes/$cm^2$, 3000 holes/$cm^2$, 4000 holes/$cm^2$, 5000 holes/$cm^2$, 6000 holes/$cm^2$, 7000 holes/$cm^2$, 8000 holes/$cm^2$, 9000 holes/$cm^2$, 10,000 holes/$cm^2$, 11,000 holes/$cm^2$, 12,000 holes/$cm^2$, 13,000 holes/$cm^2$, 14,000 holes/$cm^2$, 15,000 holes/$cm^2$, or any intermediate value. In a specific example, the density of holes is less than 10,000 holes/$cm^2$.

In variations, the hole-to-hole spacing can range from 5 micrometers to 200 micrometers or greater, and in examples, the hole-to-hole spacing is 5 micrometers, 10 micrometers, 20 micrometers, 30 micrometers, 40 micrometers, 50 micrometers, 60 micrometers, 70 micrometers, 80 micrometers, 90 micrometers, 100 micrometers, 125 micrometers, 150 micrometers, 175 micrometers, 200 micrometers, or greater. In a specific example, the hole-to-hole spacing is greater than 10 micrometers.

In variations, the membrane 120 can have a diameter or other characteristic dimension from 1 to 50 micrometers, and in examples, the diameter or other characteristic dimension can be 1 micrometer, 2 micrometers, 3 micrometers, 4 micrometers, 5 micrometers, 6 micrometers, 7 micrometers, 8 micrometers, 9 micrometers, 10 micrometers, 20 micrometers, 30 micrometers, 40 micrometers, 50 micrometers, or any intermediate value.

In examples, the hole orientation can be substantially vertical (e.g., during use in relation to a predominant gravitational force), otherwise aligned with a direction of applied force through the distribution of holes, or at another suitable angle relative to a reference plane of the membrane layer 120.

In specific examples, the thickness of the membrane layer can be from 23-125 micrometers, with a hole density of less than 10,000 holes/$cm^2$ and a hole diameter from 1 to 3 micrometers for generation of water-in-oil-in water (WOW) droplets approximately 14-30 micrometers in diameter under gravitational force of 16000 g without observation of droplet merging during formation. In the specific examples, droplets were generated form a sample volume of 50 microliters, having a fluid density of 1255 kg/$m^3$, a fluid viscosity of 0.007 Ns/$m^2$, and a surface tension of 0.07 N/m. One specific example of the membrane 120 was characterized by a membrane thickness of 125 micrometers, a hole diameter of 1.5 micrometers, a hole density of 5000/$cm^2$, an average droplet diameter of 30 micrometers, a polydispersity of ~12.1 (CV, %), under a duration of centrifugation at 16,000 g for 10 minutes.

However, other fluid compositions and characteristics can be used, such as those described in U.S. Pat. No. 11,162,136 granted on 2 Nov. 2021, which is herein incorporated in its entirety by this reference.

In relation to surface properties, the membrane layer 120 can be treated or coated with a hydrophobic material in order to provide improved consistency of droplets (e.g., in relation to consistent droplet sizes, in relation to controlled droplet sizes, in relation to monodispersity, etc.). The hydrophobic material can additionally function to improve heat stability of droplets. In variations, the hydrophobic material can include one or more of: an oil, a polysiloxane (e.g., hydroxy-terminated poly dimethylsiloxane), a fluorocarbon-coated silica with a polymer binder; a perfluoroalkyl methacrylate copolymer with our without a distribution of substrates (e.g., nanoparticle substrates); a polystyrene material (e.g., manganese oxide polystyrene, zinc oxide polystyrene), precipitated calcium carbonate, carbon nanotubes, fluorinated silanes, fluoropolymer coatings, silica-based coatings, nanocoatings, and/or other suitable hydrophobic or superhydrophobic materials. The material coating can be processed or otherwise selected to produce desired characteristics in relation to contact angle characteristics (e.g., static contact angle, contact angle hysteresis), sliding angle characteristics, and/or other suitable characteristics.

In variations, the hydrophobic/superhydrophobic material can be applied to the membrane layer 120 by one or more of: dip coating, spray coating, deposition (e.g., chemical vapor deposition), in-situ growth, polymerization, plasma coating, and/or another suitable coating technique.

Additionally or alternatively, the membrane layer 120 can include or be treated with other components or coatings to provide desired functions in relation to one or more of: electrostatic charge shielding (e.g., to prevent adsorption of proteins and other biomolecules, to improve droplet stability), protection of the membrane layer (e.g., from degradation), and/or another suitable function.

Desired droplet sizes can be produced based upon a set of factors associated with the membrane layer 120 and applied forces. Parameters of the membrane layer 120 can be improved for generation of monodisperse droplets in relation to any one or more of Weber number; other factors in relation to fluid inertia, surface tension, or other factors. In more detail with respect to Weber number, the membrane layer 120 can be configured with a suitable characteristic hole dimension D (e.g., hole depth, hole diameter), intended fluid density $\rho$, governing fluid velocity v during droplet generation, and fluid surface tension $\sigma$, where Weber number $We=\rho v^2 D/\sigma$, relating drag forces to cohesion forces in relation to droplet generation from the membrane layer. In examples, We significantly less than 1 produces periodic dripping for generation of monodisperse droplets, We~equal to 1 produces chaotic dripping for generation of polydisperse droplets, and We greater than 1 produces jetting without droplet generation. In relation to membrane parameters described above, increasing hole depth/thickness of the membrane 120 from 50 micrometers to 125 micrometers decreases the We by approximately 6.5 fold, and adjusting the hole diameter from 1 to 3 micrometers changes We from 5.7e-6 to 1.395e-3.

Relatedly, parameters associated with the membrane layer 120, fluid characteristics, and applied force characteristics can be improved for generation of droplets having a desired size. In a variation for droplet formation with an air gap between the membrane layer 120 and a collection fluid within the collecting container, droplet radius R is a function of hole radius $r_c$, surface tension of the aqueous phase $\gamma_{aq}$, fluid density of the droplet fluid $\rho_w$, and acceleration force G (e.g., associated with applied centrifugation forces, associated with pressurization, etc.), where $R\sim[[r_c\gamma_{aq}]/[2\rho_w G]]^{1/3}$.

In a variation for droplet formation without an air gap between the membrane layer 120 and a collection fluid (e.g., an oil) within the collecting container, droplet radius R is a function of hole radius $r_c$, surface tension of the interface $\gamma_{interfacial}$, fluid density of the droplet fluid $\rho_{aq}$, fluid density of the collection fluid $\rho_{oil}$, and acceleration force G (e.g., associated with applied centrifugation forces, associated with pressurization, etc.), where $R\sim[[r_c\gamma_{interfacial}]/[2(\rho_{aq}\text{-}\rho_{oil})G]]^{1/3}$.

In specific examples, the resultant droplet size can be from 10 micrometers to 80 micrometers; however, variations of the membrane layer 120 and/or system 100, as well as applied force, fluid densities of the fluid to be dropletized and the receiving fluid, interfacial tension of the fluid to be dropletized, can be configured to generate droplets with any other suitable dimensions.

2.3 System—Seals

Figure 7A:
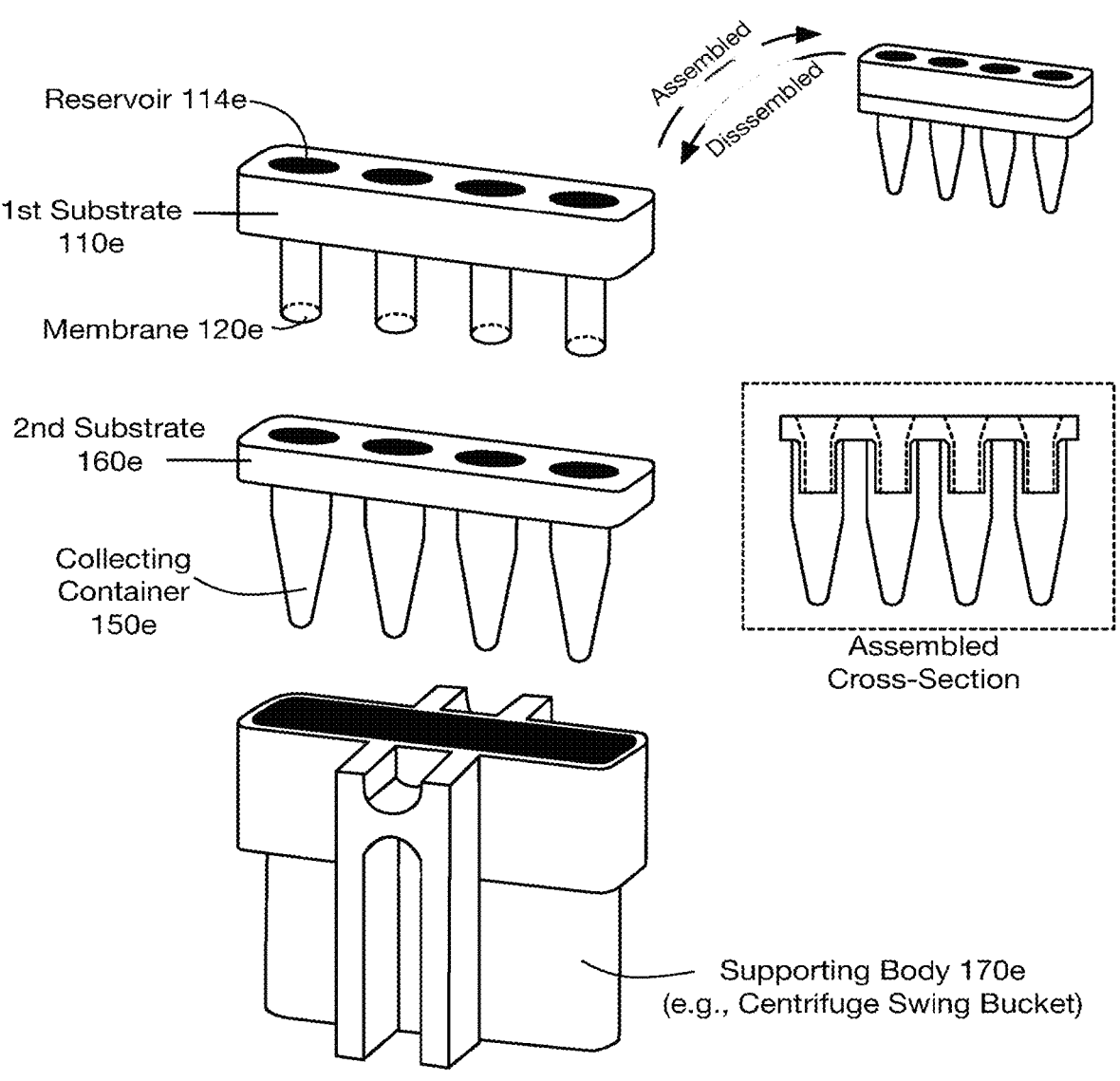
FIG. 7A depicts a second example of a system for generating droplets.
Figure 7B:
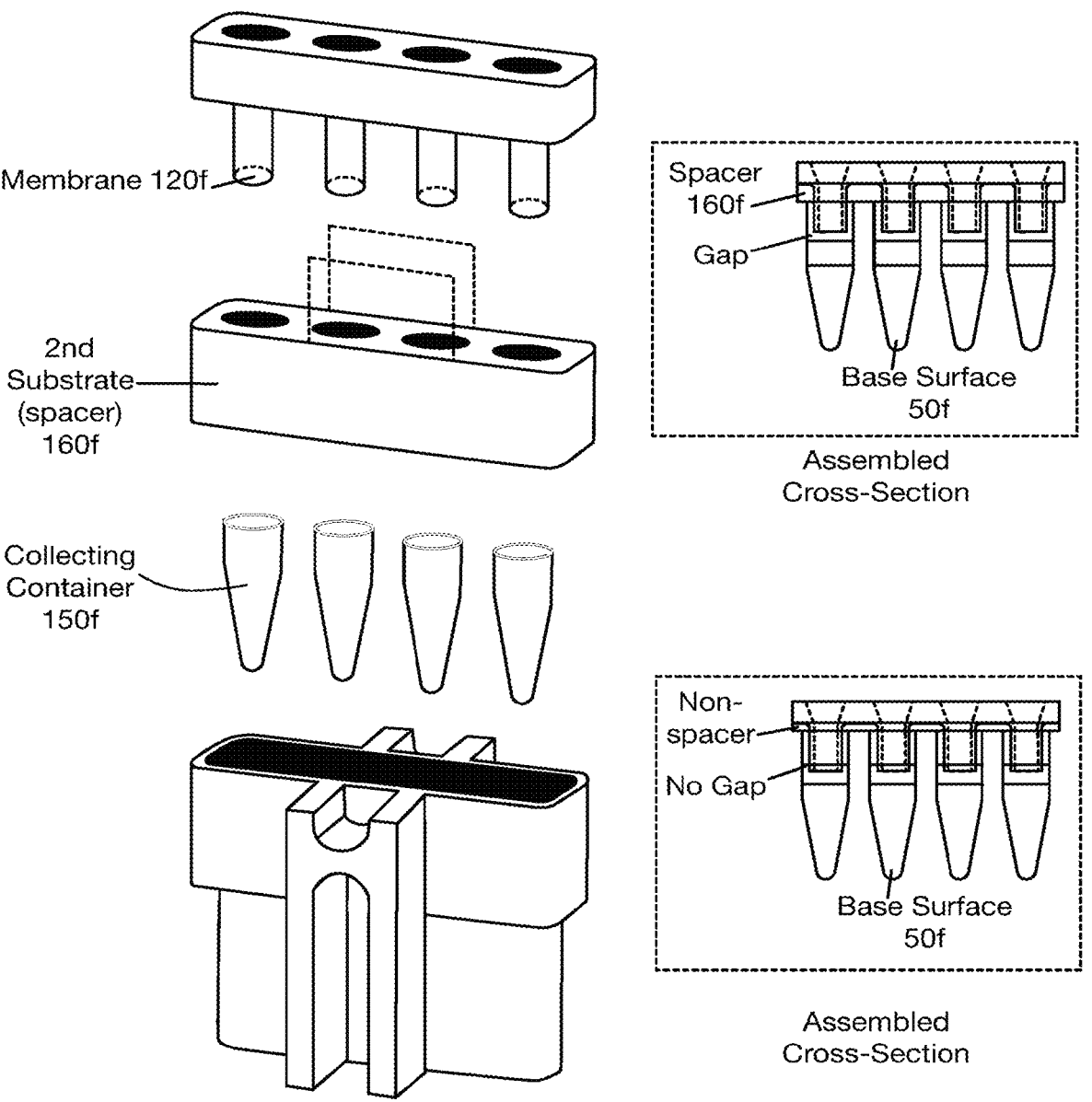
FIG. 7B depicts a third example of a system for generating droplets.

As shown in FIG. 1, the system 100 can optionally include one or more sealing bodies 130 positioned adjacent to the membrane layer 120 and including a set of openings 135 aligned with the set of reservoirs 114. The sealing body 130 functions to promote fluid transmission in a desired manner from the reservoir(s) of the first substrate 110 and through the membrane layer 120 to the collecting container(s), without leakage from the system 100 in an undesired manner. However, in some variations, the system 100 can omit a sealing body, such as in variations where the membrane layer 120 is bonded to other system elements directly, for instance, via light-curable bonding, heat bonding, or laser welding (e.g., an example of which is shown in FIGS. 7A-7B and described below in relation to FIG. 5).

Figure 6:
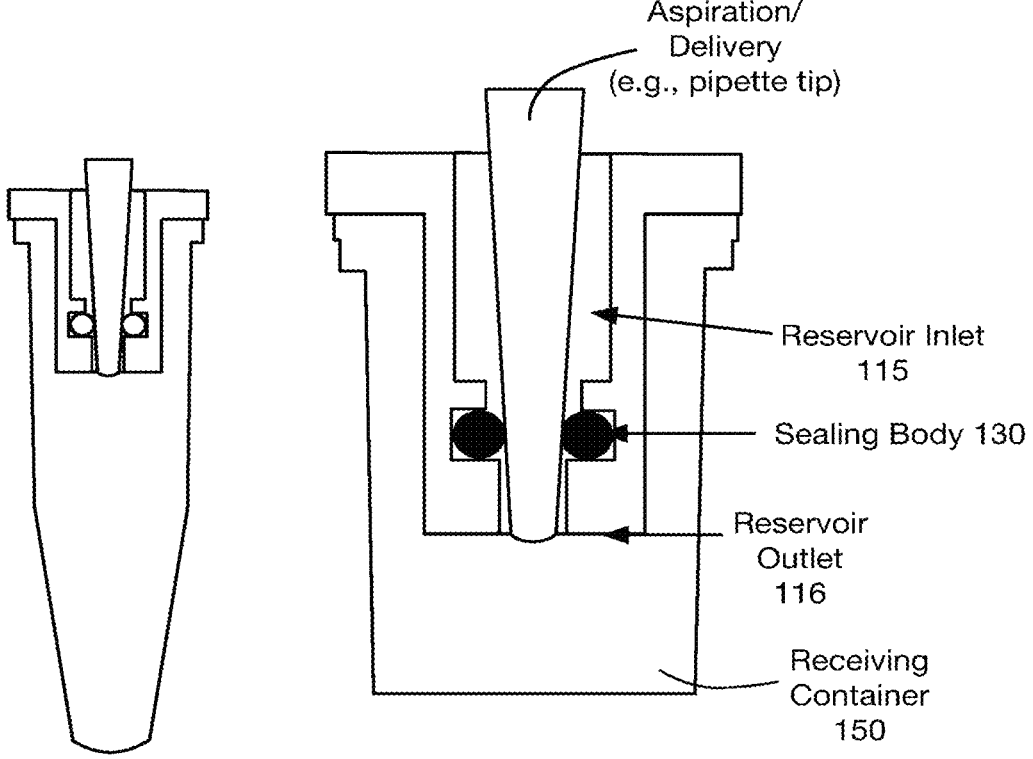
FIG. 6 depicts a variation of a configuration of a system for generating droplets.

In variations, the sealing body 130 can include a first portion upstream of the membrane layer 120. Additionally or alternatively, the sealing body 130 can include a second portion downstream of the membrane layer. In such variations, the portion(s) of sealing body 130 can be compressed or otherwise retained against the membrane layer (e.g., by way of the set of fasteners 150, the first substrate 110, and/or the second substrate 160). In these variations, the sealing body 130 portions can include or otherwise define openings aligned with and corresponding to the set of reservoirs 114 or the set of collecting containers described in more detail below. Additionally or alternatively, in a variation shown in FIG. 6, the sealing body 130 can additionally or alternatively include a portion (e.g., gasket or o-ring) positioned within a reservoir of the first substrate 110, in order to seal against a fluid delivery or pressurization device configured to drive fluid to or through the membrane layer 120 for droplet formation.

In variations, the sealing bodies 130 can include one or more of: an adhesive (e.g. optically-cured adhesive), heat-bonded seal, sealing element (e.g., o-rings, gasket, etc.), sealing film or paste, or other sealing element.

2.4 System—Fastener(s) and Collecting Container(s)

As shown in FIG. 1, the system 100 can include one or more fasteners 140 configured to retain the first substrate 110, the membrane layer 120, and the sealing body 130 in position relative to a set of collecting containers 150. The one or more fasteners 140 function to compress or otherwise retain elements of the system 100 in position properly, with respect to forces applied to the system during droplet formation.

In variations, the fasteners 140 can include one or more of: screws, pins, plungers, protrusions (e.g., tabs), recesses (e.g., recesses configured to mate with protrusions), magnetic elements, adhesives, bonded couplers (e.g., thermally bonded couplers), and/or other suitable fasteners. Variations of fasteners are shown in FIGS. 2, 3, and 4 as described above, wherein in the variation shown in FIG. 4, the fasteners 140 include protrusions that form a portion of a snap-fit mechanism with recesses of a complementary element (e.g., second substrate 110, collecting container supporting body, etc.).

As shown in FIGS. 1, 2, 6, and 7A-7C, the system 100 can be configured to complement, mate with, or otherwise interface with one or more collecting containers 150 for receiving generated droplets. FIG. 7A depicts an example of the system 100, with a set of reservoirs, including reservoir 114*e* defined within first substrate 110*e*, where a set of membranes, including membrane 120*e*, is bonded to reservoir outlets of the set of reservoirs (e.g., using the process shown and described in relation to FIG. 5). The system shown in FIG. 7A further includes second substrate 160*e*, which supports and aligns collecting containers, including collecting container 150*e*, with the set of reservoirs, such that the set of membranes is positioned within the collecting containers during use of the system. During use, the first substrate 110*e* is thus assembled with the second substrate 160*e* and collecting containers, which is positioned within supporting body 170*e* for application of a force to generate droplets.

In variations, the system 100 can be configured in a manner such that there is a gap (e.g., for air, for another fluid) between the system 100 and the collecting container(s). In such variations, one of which is shown in FIG. 7B, the second substrate can be configured as a spacer 160*f* separating the membrane 120*f* (at the respective reservoir outlet) from a base surface 50*f* of the collecting container 150*f*. As such, during droplet generation with one or more fluid layers within the collecting container 150*f*, the membrane 120*f* can be spaced above a fluid layer (FIG. 7B, top right), such that droplets generated from the membrane pass through air or other fluids prior to hitting the fluid layer. However, the substrate 160 may not be configured as a spacer, as shown in FIG. 7B (bottom right), thereby positioning the reservoir outlet 116*e* directly within a fluid layer (e.g., non-aqueous phase, oil phase, for an aqueous sample fluid) for droplet generation. As such, the system 100 can be configured in a manner such that there is no gap between the system 100 and the collecting container(s) and generated droplets are transmitted directly from the system into liquid layers within respective collecting containers.

In variations, the collecting container(s) can include any suitable number of containers with desired volumetric capacities. In examples (some of which are shown in FIGS. 7A-7C), the collecting container(s) 150 can be configured with one or more of the following formats: 0.2 ml tube format, strip tubes (e.g., 8× strip tube format), microtiter plate format (e.g., 96-well plate format, 48-well plate format, 24-well plate format, 12-well plate format, etc.), 1.5 ml tube format, conical tube format (e.g., 15 ml conical format, 50 ml conical format, etc.), or another suitable format. The collecting container(s) can be disposable or reusable. In some variations, the collecting container(s) can be supported by a supporting body 170 configured to position the system 100 properly with respect to force-applying apparatus. As shown in FIGS. 1 and 2, the collecting containers can be supported by a supporting body 170, 170*a*, respectively, which can function as a swing bucket for positioning of the system 100 within a centrifuge for force application, in order to generate droplets. However, the supporting body can be configured in another suitable manner.

The system 100 can, however, include other suitable elements for generation of droplets in a desired manner. Furthermore, the system 100 can be configured to transition between various operation modes, including: a first operation mode wherein the first substrate is coupled with the second substrate and encloses the collecting container, with the reservoir outlet seated within the collecting container (an example of which is shown in FIG. 7A), a second operation mode wherein the reservoir contains a sample fluid (an embodiment of which is shown in FIG. 1), and a third operation mode wherein the membrane generates a plurality of droplets within the collecting container at a high rate (e.g., of at least 1 million droplets per minute, at other rates described) in response to a force applied to the sample fluid, and a fourth operation mode wherein the plurality of droplets is stabilized in position in a close-packed format within a region of the collecting container. In relation to the operation modes described, structural configurations of the system or contents of the system can produce droplets with a low degree of polydispersity (e.g., less than 15% coefficient of variation for polydispersity, less than 14% coefficient of variation for polydispersity, less than 13% coefficient of variation for polydispersity, less than 12% coefficient of variation for polydispersity, less than 11% coefficient of variation for polydispersity, less than 10% coefficient of variation for polydispersity, less than 9% coefficient of variation for polydispersity, less than 8% coefficient of variation for polydispersity, less than 7% coefficient of variation for polydispersity, less than 6% coefficient of variation for polydispersity, less than 5% coefficient of variation for polydispersity, etc.) at an unprecedented rate, for digital analyses and other applications, as described above.

As such, generating the plurality of droplets can include driving the aqueous mixture through a distribution of holes of a membrane (e.g., track-etched membrane) to stabilized positions toward a closed end of the collecting container, the plurality of droplets having significantly low polydispersity, as described above.

Aspects of methods performed by embodiments, variations, and examples of the system 100 described in more detail below.

3. Methods

As shown in FIG. 8, an embodiment of a method 200 for generation of droplets may include: generating a plurality of droplets within a collecting container at a high rate, each of the plurality of droplets including an aqueous mixture for a digital analysis S210. In embodiments, upon generation, the plurality of droplets is stabilized in position in a close-packed format (e.g., three-dimensional close-packed format, hexagonal close-packed format, rectangular close-packed format, etc.) within a continuous phase, within a region of the collecting container S220.

Embodiments of the method 200 may function to generate a plurality of droplets at an extremely high and unprecedented rate in the context of digital analyses and other assays, where the droplets are stabilized in position (e.g., in a close-packed format, in equilibrium stationary positions) within a collecting container. Embodiments of the method 100 may further function to reliably generate droplets in a consistent and controlled manner (e.g., as monodisperse and uniform droplets having little-to-no polydispersity) for various applications, such as digital amplification and analysis and other assays; capture of target material at cellular, subcellular, and molecular scales; sample analysis benefitting from droplet generation; and/or other suitable applications. Embodiments of the method may function to generate droplets using devices that are non-microfluidic, disposable or reusable, in a cost-effective manner.

Embodiments, variations, and examples of the method 200 can be implemented by or by way of embodiments, variations, and examples of components of the system 100 described in Section 2 above. However, the method 200 can additionally or alternatively be configured to perform other suitable methods.

3.1 Methods—Droplet Generation

In relation to generation of droplets at a high rate in Step S210, variations of the method 200 can produce droplets at a rate of at least 200,000 droplets/minute, of at least 300,000 droplets/minute, of at least 400, droplets/minute, of at least 500,000 droplets/minute, of at least 600,000 droplets/minute, of at least 700,000 droplets/minute, of at least 800,000 droplets/minute, of at least 900,000 droplets/minute, of at least 1 million droplets/minute, of at least 2 million droplets/minute, of at least 3 million droplets/minutes, or greater, using embodiments, variations, and examples of system elements described above. Droplets can be generated at the high rate, using embodiments, variations, and examples of the membrane(s) 120 described above, in relation to hole density, hole-to-hole spacing, hole diameter, membrane thickness, hole aspect ratio, membrane material, and/or other characteristics.

In relation to droplet generation in Step S210, an extremely high number of droplets can be generated within a collecting container, wherein, in variations, greater than 2 million droplets, greater than 3 million droplets, greater than 4 million droplets, greater than 5 million droplets, greater than 6 million droplets, greater than 7 million droplets, greater than 8 million droplets, greater than 9 million droplets, greater than 10 million droplets, greater than greater than 15 million droplets, greater than 20 million droplets, greater than 25 million droplets, greater than 30 million droplets, greater than 40 million droplets, greater than 50 million droplets, greater than 100 million droplets, greater than 200 million droplets, greater than 300 million droplets, or greater can be generated within the collecting container.

In variations, the collecting container can have a volumetric capacity less than 50 microliters or from 50 through 300 microliters and greater. An example of a collecting container can include a PCR strip tube having a volumetric capacity from 20 microliters to 50 microliters; however, other variations and examples of collecting containers are described in more detail in Section 2 above. Droplets generated in Step S210 may have a characteristic dimension (e.g., from 1-50 micrometers, from 10-30 micrometers, intermediate values within ranges described, etc.) that is relevant for digital analyses, single cell capture, target detection, individual molecule partitioning, or other applications.

Generating the plurality of droplets in Step S210 can include driving a sample fluid through a membrane comprising a distribution of holes, the membrane aligned with or coupled to a reservoir outlet of a reservoir for the sample fluid. Driving the sample fluid can include applying a centrifugal force (e.g., by centrifugation) to drive the sample fluid through the holes of the membrane. In variations, the centrifugal force can be applied at 1,000 g, 2,000 g, 3,000 g, 4,000 g, 5,000 g, 6,000 g, 7,000 g, 8,000 g, 9,000 g, 10,000 g, 11,000 g, 12,0000 g, 13,000 g, 14,000 g, 15,000 g, 16,000 g, 17,000 g, 18,000 g, 19,000 g, 20,000 g, 30,000 g, any intermediate value, or greater than 30,000 g. Duration of spinning can be 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 30 minutes, 40 minutes, 50 minutes, any intermediate value, or greater than 50 minutes, where spin duration is a function of the amount of sample fluid being dropletized according to methods described.

In relation to generation of droplets of an emulsion (e.g., by driving sample fluids through one or more immiscible layers of fluid to form a multi-phase emulsion), where resultant emulsions generated have viscous properties, shear-thickening properties, and/or gel-like properties (e.g., as is present when generating emulsions where droplets are a first phase surrounded by films of a second phase that is immiscible with the first phase, and droplets are surrounded by a continuous third phase that is immiscible with the third phase), centrifugation can produce emulsions having uneven top/superior surface (e.g., surfaces furthest away from a base of the collecting container, along a force axis in a radial direction attributed to centrifugation), an example of which is shown in FIG. 9A. Such uneven surfaces can increase difficulty of readout of signals from droplets near the top/superior surface (e.g., emulsion surface furthest from the base of the collecting container), due to higher background, reduced clarity, and/or other factors.

As such, the method 200 can further include S214, which, as shown in FIG. 9B involves spinning the sample fluid, the membrane, and the collecting container within a centrifuge in a first direction of rotation, and reversing the direction of rotation, thereby adjusting a surface profile of an emulsion comprising the plurality of droplets within the collecting container. Adjusting the surface profile can improve one or more of levelness, planarity, or other characteristics of the surface profile to improve readout ability. In relation to S214, spinning in the first direction and the second direction can be performed at centrifugal forces in the ranges provided above or outside described ranges. Furthermore, spinning in the first direction can be performed at a first rotational velocity, and spinning in the second direction can be performed at a second rotational velocity different than the first rotational velocity.

Additionally or alternatively, the method 200 can further include S216, which as shown in FIG. 9C, involves spinning the sample fluid, the membrane, and the collecting container within a centrifuge at a first rotational velocity and at a second rotational velocity less than the first rotational velocity, thereby adjusting a surface profile of an emulsion comprising the plurality of droplets within the collecting container. Adjusting the surface profile can improve one or more of levelness, planarity, or other characteristics of the surface profile to improve readout ability. In relation to S216, spinning at the first rotational velocity and the second rotational velocity can be performed at centrifugal forces in the ranges provided above or outside described ranges. Furthermore, in relation to Steps S214 and S216, achieving the first rotational velocity and/or the second rotational velocity can be performed with a ramp-up or acceleration rate, in order to improve surface features of the emulsion.

In alternative variations, the applied force can be associated with an applied pressure, magnetically applied, or otherwise physically applied to drive sample fluid(s) through the membrane(s).

In relation to components of the sample fluid and/or fluid layers within the collecting container(s) for generation of an emulsion, the sample fluid and fluid layers within the collecting container can have one or more of a certain density, viscosity, surface tension, aqueous nature, hydrophobicity, immiscibility characteristics, or other characteristics. Fluids implemented can have densities from 1 through 3000 $kg/m^3$ and intermediate values, viscosities from 0.001 through 0.1 $Ns/m^2$, and surface tensions of 0.01 through 1 N/m, depending upon application. Sample fluids and/or fluid layers can further include materials described in U.S. Pat. No. 11,162,136 granted on 2 Nov. 2021, incorporated by reference above. As such, droplets and/or resulting emulsions generated with said droplets can have a high degree and greater than a threshold level of clarity, with or without refractive index matching. In variations, the threshold level of clarity of the emulsion is associated with a transmissivity greater than 50% transmissivity, greater than 60% transmissivity, greater than 70% transmissivity, greater than 80% transmissivity, greater than 90% transmissivity, greater than 95% transmissivity, greater than 99% transmissivity, etc., upon measuring clarity of the emulsion using a transmission detector.

In embodiments, upon generation, the plurality of droplets may be stabilized in position in a close-packed format (e.g., three-dimensional close-packed format, hexagonal close-packed format, rectangular close-packed format, etc.) within a continuous phase, within a region of the collecting container S220. In relation to the membranes described, generating the plurality of droplets can include transmitting droplets (e.g., two dimensional arrays of droplets from the holes of the membrane(s)) toward a closed end of the collecting container, thereby stabilizing the plurality of droplets in a three dimensional close-packed format toward the closed end of the collecting container. Alternatively, the plurality of droplets can be stabilized (e.g., within a continuous phase, within a matrix positioned within the collecting container, within a mesh within the collecting container, etc.) toward the closed end or a different region of the collecting container, in a non-close-packed format. For instance, non-close packed droplets or droplets that can move relative to each other within the closed collecting container can still be processed by optical interrogation as described in more detail in Section 3 below (e.g., by fixing a position of the closed collecting container relative to a scanning path of an optical interrogation instrument). Additionally or alternatively, in relation to close-packed or non-close-packed formats, droplets of an emulsion can be stabilized in position by curing (e.g., with light, with heat, with a pH shift, with other cross-linking, by way of an electric field, by way of a magnetic field, etc.) the dispersed phase, continuous phase, or both of the emulsion. Still alternatively, droplets may not be stabilized in position or in a close-packed format (e.g., droplets can move relative to each other within a container, such as for water-in-oil or oil-in-water emulsions, etc.).

In some variations, as shown in FIG. 8, the method 200 can further include: transmitting heat to and from the plurality of droplets, within the collecting container, during a heat transmission operation S230. Heat transmission can be associated with cold storage (e.g., refrigeration, freezing, etc.), thermocycling (e.g., during an amplification process), etc.), incubation, lysis, enzyme activation, or another heat transmission operation. In variations, the temperature may vary between 0° C. to 95° C. during the heat transmission operation, and in specific examples, the temperature can transition between temperatures within the ranges described, with stability of droplets maintained. In particular, given the droplet generation techniques and materials described, individual droplets of the plurality of droplets remain unmerged with adjacent droplets in the close-packed format during the heat transmission operation.

In some variations, as shown in FIG. 8, the method 200 can further include: performing an optical interrogation operation with the plurality of droplets within the collecting container S240, where the optical interrogation operation can include readout of signals (e.g., light signals, fluorescent signals, colorimetric signals, etc.) from droplets of the plurality of droplets. In particular, readout can be performed for cross sections of the plurality of droplets within the collecting container, using techniques described in applications incorporated by reference.

In variations, readout of fluorescent signals (e.g., from labeled analytes within droplets of the dispersed phase, from products of analytes within droplets of the dispersed phase, etc.) can be performed by one or more of a 3D scanning technique (e.g., light sheet imaging, confocal microscopy, etc.) and a planar imaging technique (e.g., to take images of a cross-section of the closed container). Additionally or alternatively, in a some applications, readout of colorimetric changes associated with droplets of the dispersed phase can be performed by 3D imaging techniques (e.g., 3D brightfield construction using light field imaging, etc.). Readout can be performed for each of a set of cross sections of the plurality of droplets/collecting container, across multiple color channels (e.g., 2 color channels, three color channels, four color channels, five color channels, six color channels, seven color channels, etc.).

Readout can be performed for 10 cross-sections of the plurality of droplets, 20 cross-sections of the plurality of droplets, 30 cross-sections of the plurality of droplets, 40 cross-sections of the plurality of droplets, 50 cross-sections of the plurality of droplets, 60 cross-sections of the plurality of droplets, 70 cross-sections of the plurality of droplets, 80 cross-sections of the plurality of droplets, 90 cross-sections of the plurality of droplets, 100 cross-sections of the plurality of droplets, 200 cross-sections of the plurality of droplets, 300 cross-sections of the plurality of droplets, 400 cross-sections of the plurality of droplets, 500 cross-sections of the plurality of droplets, 600 cross-sections of the plurality of droplets, any intermediate value, or greater, within the closed collecting container, for each of the set of color channels.

In specific examples, readout associated with digital analyses (e.g., counting, quantification, etc.) for each channel can be performed within a duration of 5 minutes, 4 minutes, 3 minutes, 2 minutes, 1 minute, 30 seconds, 20 seconds, 10 seconds, or less, depending upon one or more of signal-to-noise ratio, optical sensor sensitivity, excitation power (e.g., of a light source used to illuminate droplets and induce fluorescence), or other characteristics.

In other variations, readout of non-fluorescent signals from droplets of the dispersed phase can be performed. For instance, products resulting from reactions within individual droplets of the dispersed phase can produce changes in one or more of refractive indices, light absorption, light scattering, light reflection, light transmission, or other light interaction characteristics that are different from empty or unreacted droplets, for detection by various techniques (e.g., spectrophotometric techniques, turbidimetric techniques, etc.).

As such, methods described enable digital analyses across a wide dynamic range that is 10-100 times greater than that of existing technologies, depending upon application of use. In examples related to nucleic acid counting, the methods disclosed herein can have a dynamic range from 1 through 100 million, due to the extremely high number of uniform partitions generated from which signals can be read, and due to the ability to partition with low occupancy (e.g., less than 20% occupancy, less than 15% occupancy, less than 10% occupancy, less than 9% occupancy, less than 8% occupancy, less than 7% occupancy, less than 6% occupancy, less than 5% occupancy, etc.) of partitions by targets. In variations, such low occupancy can enable characterization of targets of interest without requiring Poisson statistics-associated correction factors for partitioning error or other error.

In examples, generation of large numbers of droplets (as described) within a closed container can be performed within durations and at rates described (e.g., on the order of 1 million droplets/minute), and readout of each channel for a digital analysis can be performed at a high rate (e.g., less than 1 minute per channel, across multiple color channels), thereby enabling readout for a digital analysis of millions of partitions on the order of minutes or hours (with time durations described as above).

As such, methods for droplet generation through readout of numbers of droplets described, for each of a set of channels for a digital analysis, can be performed within a duration of 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 20 minutes, 25 minutes, 30 minutes, 35 minutes, 40 minutes, 45 minutes, 50 minutes, 55 minutes, 1 hour, 2 hours, 3 hours, 4 hours, or any intermediate value. In examples, once droplet generation and amplification/tagging have been performed, readout of signals from each channel can be performed within 5 minutes, 4 minutes, 3 minutes, 2 minutes, 1 minute, 30 seconds, 20 seconds, 10 seconds, or less, depending upon one or more of signal-to-noise ratio, optical sensor sensitivity, excitation power (e.g., of a light source used to illuminate droplets and induce fluorescence), or other characteristics.

As such, methods for droplet generation through readout of numbers of droplets can include: performing a digital analysis of target nucleic acid material from a sample within a duration (e.g., a duration described), wherein performing the digital analysis includes: generating a plurality of droplets (e.g., within a closed collecting container, the plurality of droplets comprising a number of droplets described generated from a combination of the sample and materials for an amplification reaction, individually isolating the plurality of droplets (e.g., within a continuous phase of an emulsion), receiving heat (e.g., through the closed collecting container), thereby amplifying said target nucleic acid material, and transmitting signals, (e.g., from a set of cross-sections of the emulsion comprising the plurality of droplets within the closed collecting container), for readout using a set of channels of a detection system (e.g., a detection system interacting with the closed collecting container).

3.1.1 Method—Implementation

As shown in FIG. 10, an embodiment of a method 300 for generation of droplets includes: providing an assembly S310 including: a first substrate defining one or more reservoirs, a membrane layer including a distribution of holes positioned downstream of the one or more reservoirs, one or more sealing bodies positioned adjacent to the membrane layer and including a set of openings aligned with the set of reservoirs, and optionally one or more fasteners configured to retain the assembly in position relative to one or more collecting containers containing a first fluid; optionally, receiving a second fluid into the one or more reservoirs S320, wherein the second fluid is intended for use in droplet formation and is immiscible with the first fluid; and applying force (e.g., centrifugation, pressurization, etc.) to contents of the reservoirs/assembly S330, thereby driving the second fluid from the one or more reservoirs, through the membrane layer, and into the one or more collecting containers.

Embodiments of the method 300 function to reliably generate monodisperse droplets for various applications (as described above, and at rates described above), such as digital amplification; capture of target material at cellular, subcellular, and molecular scales; sample analysis benefitting from droplet generation; or other suitable applications.

Embodiments of the method 300 can also function to generate monodisperse droplets using devices that are non-microfluidic, disposable, or reusable, in a cost-effective manner.

In specific applications, the method 300 can be used to generate droplets with applications in one or more of: emulsion generation (e.g., single emulsion generation, double emulsion generation), microparticle generation, liposome generation, hydrogel microparticle generation, nucleic acid amplification (e.g., by polymerase chain reaction (PCR) methods, by isothermal methods such as loop-mediated isothermal amplification (LAMP), by recombinase polymerase amplification (RPA), by multiple displacement amplification (MDA), by helicase dependent amplification (HDA), by strand displacement amplification (SDA), by nicking enzyme amplification (NEAR), by transcription mediated amplification (TMA), by digital helicase dependent amplification, by RNaseH mediated amplification, by whole genome amplification (WGA), by rolling circle amplification, etc.) on purified DNA, cDNA, RNA, or directly from lysate (e.g., blood lysate); fluorescent in situ hybridization (FISH) with fluorescently tagged nucleic acids (e.g., PNA, LNA, DNA, RNA, etc.) or an indirect in situ hybridization approach using DIG or biotin; by an in vitro transcription or translation assay (e.g., whereby a colorimetric or fluorescent reporter is used for detection); droplet PCR applied to samples derived from single cells (e.g., prokaryotes, eukaryotes), organelles, viral particles, and exosomes; droplet analysis of proteins (e.g., by proximity ligation assays, etc.); sequencing applications (e.g., single molecule sequencing applications); monitoring or detection of products (e.g., proteins, chemicals) released from single cells (e.g., interleukin released from immune cells); monitoring cell survival and/or division for single cells; monitoring or detection of enzymatic reactions involving single cells; target material capture at cellular (e.g., mammalian cell, bacterial cell, pathogen, viral, etc.) and sub-cellular (e.g., organelle, molecular, etc.) scales; enumeration of heterogeneous cell populations in a sample; enumeration of individual cells or viral particles (e.g., by encapsulating cells in droplets with species-specific antibodies coupled with enzymes that react with substrate components in the droplet to produce signals, etc.); monitoring of viral infections of a single host cell; and other suitable applications.

The method 300 can be implemented by an embodiment, variation, or example of the system 100 described above, or can alternatively be implemented by another suitable system.

4. Computer Systems

Figure 11:
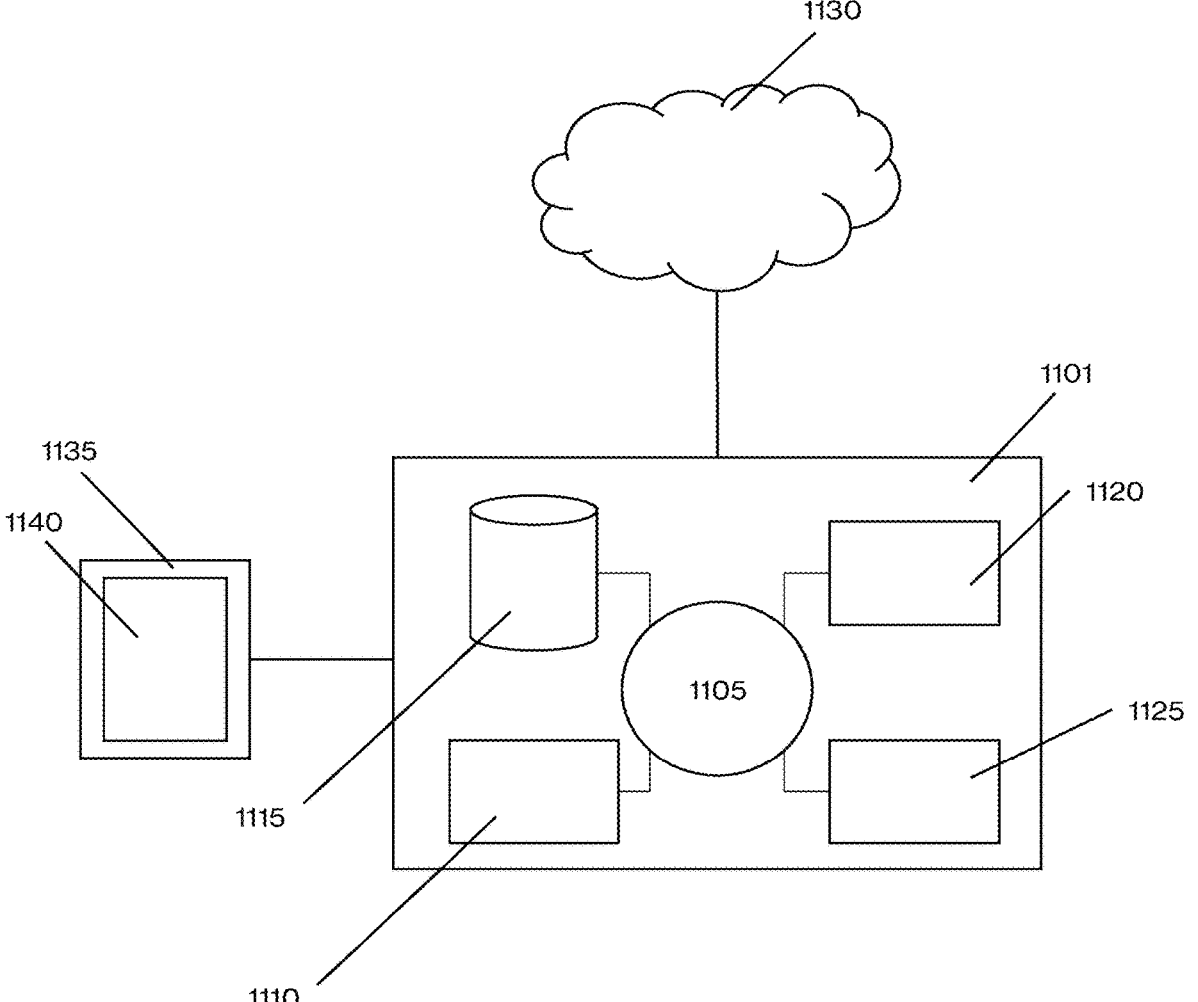
FIG. 11 illustrates a computer system that is programmed or otherwise configured to implement methods provided herein.

The present disclosure provides computer systems that are programmed to implement methods of the disclosure. FIG. 11 shows a computer system 1101 that is programmed or otherwise configured to, for example, generate a plurality of droplets within a collecting container at a predetermined rate or variation in polydispersity, transmit heat to and from the plurality of droplets within the collecting container, or perform an optical interrogation operation with the plurality of droplets within the collecting container.

The computer system 1101 can regulate various aspects of analysis, calculation, and generation of the present disclosure, such as, for example, generating a plurality of droplets within a collecting container at a predetermined rate or variation in polydispersity, transmitting heat to and from the plurality of droplets within the collecting container, or performing an optical interrogation operation with the plurality of droplets within the collecting container. The computer system 1101 can be an electronic device of a user or a computer system that is remotely located with respect to the electronic device. The electronic device can be a mobile electronic device.

The computer system 1101 includes a central processing unit (CPU, also "processor" and "computer processor" herein) 1105, which can be a single core or multi core processor, or a plurality of processors for parallel processing. The computer system 101 also includes memory or memory location 1110 (e.g., random-access memory, read-only memory, flash memory), electronic storage unit 1115 (e.g., hard disk), communication interface 1120 (e.g., network adapter) for communicating with one or more other systems, and peripheral devices 1125, such as cache, other memory, data storage and/or electronic display adapters. The memory 1110, storage unit 1115, interface 1120 and peripheral devices 1125 are in communication with the CPU 1105 through a communication bus (solid lines), such as a motherboard. The storage unit 1115 can be a data storage unit (or data repository) for storing data. The computer system 1101 can be operatively coupled to a computer network ("network") 1130 with the aid of the communication interface 1120. The network 1130 can be the Internet, an internet and/or extranet, or an intranet and/or extranet that is in communication with the Internet.

In some embodiments, the network 1130 is a telecommunication and/or data network. The network 1130 can include one or more computer servers, which can enable distributed computing, such as cloud computing. For example, one or more computer servers may enable cloud computing over the network 1130 ("the cloud") to perform various aspects of analysis, calculation, and generation of the present disclosure, such as, for example, generating a plurality of droplets within a collecting container at a predetermined rate or variation in polydispersity. Such cloud computing may be provided by cloud computing platforms such as, for example, Amazon Web Services (AWS), Microsoft Azure, Google Cloud Platform, and IBM cloud. In some embodiments, the network 1130, with the aid of the computer system 1101, can implement a peer-to-peer network, which may enable devices coupled to the computer system 101 to behave as a client or a server.

The CPU 1105 may comprise one or more computer processors and/or one or more graphics processing units (GPUs). The CPU 1105 can execute a sequence of machine-readable instructions, which can be embodied in a program or software. The instructions may be stored in a memory location, such as the memory 1110. The instructions can be directed to the CPU 1105, which can subsequently program or otherwise configure the CPU 1105 to implement methods of the present disclosure. Examples of operations performed by the CPU 1105 can include fetch, decode, execute, and writeback.

The CPU 1105 can be part of a circuit, such as an integrated circuit. One or more other components of the system 1101 can be included in the circuit. In some embodiments, the circuit is an application specific integrated circuit (ASIC).

The storage unit 1115 can store files, such as drivers, libraries and saved programs. The storage unit 1115 can store user data, e.g., user preferences and user programs. In some embodiments, the computer system 1101 can include one or more additional data storage units that are external to the computer system 1101, such as located on a remote server that is in communication with the computer system 1101 through an intranet or the Internet.

The computer system 1101 can communicate with one or more remote computer systems through the network 1130. For instance, the computer system 1101 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iphone, Android-enabled device, Blackberry®), or personal digital assistants. The user can access the computer system 101 via the network 1130.

Methods as described herein can be implemented by way of machine (e.g., computer processor) executable code stored on an electronic storage location of the computer system 1101, such as, for example, on the memory 1110 or electronic storage unit 1115. The machine executable or machine readable code can be provided in the form of software. During use, the code can be executed by the processor 1105. In some embodiments, the code can be retrieved from the storage unit 1115 and stored on the memory 1110 for ready access by the processor 1105. In some situations, the electronic storage unit 1115 can be precluded, and machine-executable instructions are stored on memory 1110.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Embodiments of the systems and methods provided herein, such as the computer system 1101, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, or disk drives, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1101 can include or be in communication with an electronic display 135 that comprises a user interface (UI) 1140 for providing, for example, a visual display indicative of generating a plurality of droplets within a collecting container at a predetermined rate or variation in polydispersity, transmitting heat to and from the plurality of droplets within the collecting container, or performing an optical interrogation operation with the plurality of droplets within the collecting container. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 1105. The algorithm can, for example, generate a plurality of droplets within a collecting container at a predetermined rate or variation in polydispersity.

5. Conclusions

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or, if applicable, portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams or flowchart illustration, and combinations of blocks in the block diagrams or flowchart illustration, can be implemented by special purpose hardware-based systems that perform the specified functions or acts, or combinations of special purpose hardware and computer instructions.

It should be understood from the foregoing that, while particular implementations have been illustrated and described, various modifications may be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents. It is intended that the following claims define the scope of the invention and that methods and structures within the scope of these claims and their equivalents be covered thereby.

What is claimed is:

1. A method comprising:
   (a) providing a sample comprising a set of target nucleic acid molecules, wherein the sample has a volume of less than 50 microliters;
   (b) generating a set of droplets comprising processing materials and the set of target nucleic acid molecules of the sample within a duration of 50 minutes, wherein the set of droplets comprises at least 500,000 droplets, wherein a droplet of the set of droplets is surrounded by an immiscible fluid in a continuous phase immiscible with the immiscible fluid, wherein the set of droplets has a polydispersity coefficient of variation of less than 10%;
   (c) collecting the set of droplets within a collecting container;
   (d) amplifying the set of target nucleic acids or derivatives thereof within the collecting container; and
   (e) scanning the set of droplets to detect signals corresponding to the set of target nucleic acid molecules or derivatives thereof.

2. The method of claim 1, wherein (b) is performed within a duration of 40 minutes.

3. The method of claim 1, wherein the set of droplets comprises at least 1 million droplets.

4. The method of claim 1, wherein the set of droplets has a polydispersity coefficient of variation of less than 5%.

5. The method of claim 1, wherein (e) comprises scanning droplets of the set of droplets across a set of channels comprising at least two color channels.

6. The method of claim 1, wherein (e) comprises scanning droplets of the set of droplets across a set of channels comprising at least four color channels.

7. The method of claim 1, wherein (e) comprises scanning droplets of the set of droplets across a set of channels comprising at least six color channels.

8. The method of claim 1, wherein (e) comprises scanning droplets of the set of droplets across a set of channels comprising at least seven color channels.

9. The method of claim 1, wherein the set of target nucleic acid molecules comprises deoxyribonucleic acid (DNA) molecules.

10. The method of claim 1, wherein the set of target nucleic acid molecules comprises ribonucleic acid (RNA) molecules.

11. The method of claim 1, wherein the set of target nucleic acid molecules comprises viral target nucleic acid molecules.

12. The method of claim 1, wherein the sample comprises biological material collected from a human subject.

13. The method of claim 1, wherein the sample comprises biological material collected from multiple human subjects.

14. A method comprising:

(a) providing a sample comprising a set of targets, wherein the sample has a volume of less than 50 microliters;

(b) generating a set of droplets comprising processing materials and the set of targets of the sample within a duration of 50 minutes, wherein the set of droplets comprises at least 1,000,000 droplets, wherein a droplet of the set of droplets is surrounded by an immiscible fluid in a continuous phase immiscible with the immiscible fluid, wherein the set of droplets has a polydispersity coefficient of variation of less than 5%;

(c) collecting the set of droplets within a collecting container;

(d) amplifying the set of targets or derivatives thereof within the collecting container; and (e) scanning cross sections of droplets containing the set of targets across a set of at least four channels, thereby detecting signals corresponding to the set of targets or derivatives thereof.

15. The method of claim 14, wherein (a) through (d) are completed within a duration of four hours.

16. The method of claim 14, wherein the set of targets comprises nucleic acid targets.

17. The method of claim 14, wherein the set of targets comprises viral targets.

18. The method of claim 14, wherein the set of targets comprises protein targets.

19. A method comprising:

(a) distributing a set of targets across a set of partitions comprising at least one million partitions, wherein a partition of the set of partitions comprises a hydrogel and is surrounded by an immiscible layer in a continuous phase immiscible with the immiscible layer;

(b) collecting the set of partitions within a collecting container;

(c) amplifying nucleic acids associated with the set of targets or derivatives thereof within the collecting container; and (d) performing optical interrogation of sequences corresponding to the set of targets or derivatives thereof, thereby detecting signals corresponding to the set of targets or derivatives thereof.

20. The method of claim 19, wherein the set of targets or derivatives thereof comprises nucleic acid targets.

21. The method of claim 19, wherein the set of targets or derivatives thereof comprises single cell targets.

22. The method of claim 19, before (d), further comprising performing an enzymatic reaction involving single cells within the set of partitions in coordination with amplifying nucleic acids in (c).

23. The method of claim 19, wherein the set of partitions is generated using a set of channels.

\* \* \* \* \*